(12) United States Patent
Ikeda et al.

(10) Patent No.: US 8,758,689 B2
(45) Date of Patent: Jun. 24, 2014

(54) REACTION ANALYSIS APPARATUS, RECORDING MEDIUM, MEASUREMENT SYSTEM AND CONTROL SYSTEM

(75) Inventors: Yuji Ikeda, Kobe (JP); Atsushi Nishiyama, Kobe (JP)

(73) Assignee: Imagineering, Inc., Kobe-Shi Hyogo (JP)

( * ) Notice: Subject to any disclaimer, the term of this patent is extended or adjusted under 35 U.S.C. 154(b) by 1443 days.

(21) Appl. No.: 12/514,533

(22) PCT Filed: Nov. 17, 2007

(86) PCT No.: PCT/JP2007/072329
§ 371 (c)(1),
(2), (4) Date: May 12, 2009

(87) PCT Pub. No.: WO2008/059976
PCT Pub. Date: May 22, 2008

(65) Prior Publication Data
US 2010/0055001 A1  Mar. 4, 2010

(30) Foreign Application Priority Data
Nov. 17, 2006  (JP) .................................. 2006-323030

(51) Int. Cl.
*G01N 21/00* (2006.01)
(52) U.S. Cl.
USPC ........................................ 422/82.05; 700/266
(58) Field of Classification Search
CPC .................................................... H01J 49/0027
USPC ............ 700/59, 266; 422/82.05; 356/47, 326; 436/171, 172, 805
See application file for complete search history.

(56) References Cited

U.S. PATENT DOCUMENTS 3,728,029 A * 4/1973 Hirschfeld .................... 356/308

FOREIGN PATENT DOCUMENTS

| JP | 62-276421 | 12/1987 |
| JP | 11-166722 | 6/1999 |
| JP | 2000-179843 | 6/2000 |
| JP | 2005-164128 | 6/2005 |
| JP | 2005-226893 | 8/2005 |
| JP | 2006-292524 | 10/2006 |

OTHER PUBLICATIONS

Yuji Ikeda et al., "Methane • Kuki Oyobi Propane • Kukisoryu Yokongo Kaen no Kyokusho Jihakko Spectrum Keisoku", Jan. 25, 2003, pp. 200-206, vol. 69, No. 677, Transactions of the Japan Society of Mechanical Engineers, Series B.

* cited by examiner

*Primary Examiner* — Natalia Levkovich
(74) *Attorney, Agent, or Firm* — Bacon & Thomas, PLLC

(57) ABSTRACT

The present invention is capable of determining that a reaction region is in an abnormal reaction state precisely with high reproducibility, executing proper analysis processing in accordance with the determined a state of the reaction region, and efficiently analyzing a characteristic of the reaction region. The present invention obtains intensity values of first and second wavelength components by measurement of light emitted from the reaction region with a spectrometer. A relative intensity calculator calculates relative intensity of the first wavelength component relative to the second wavelength component from the intensity values of the first and second wavelength components. The apparatus determines whether or not the calculated relative intensity is a value within a predetermined range. An output portion provides notification that the state of the reaction region is a predetermined state when it is determined that the relative intensity is within the predetermined range.

4 Claims, 13 Drawing Sheets

REACTION ANALYSIS APPARATUS, RECORDING MEDIUM, MEASUREMENT SYSTEM AND CONTROL SYSTEM

TECHNICAL FIELD

The present invention relates to a reaction analysis apparatus and a measurement system for measuring and analyzing a state of a reaction such as a combustion reaction and a plasma reaction (hereinafter, simply referred to as the "reaction"), particularly to a reaction analysis apparatus for detecting and notifying generation of soot, a luminous flame, a non-premixed flame such as fuel premixing failure and a diffusion flame, breakdown due to an input of high energy to a reaction region and the like, and obtaining information from the reaction region by an optical measurement method so as to analyze a characteristic of the reaction based on the information, a measurement system, and a control system. The present invention also relates to a recording medium in which a program for forming the reaction analysis apparatus is recorded.

BACKGROUND ART

When an abnormal reaction occurs in a region where a reaction occurs (hereinafter, simply referred to as the "reaction region"), and unreacted particles are mixed or the reaction becomes incomplete, there is a large influence on an action of an engine of operating with utilizing the reaction. For example, in the case where premixing of hydrocarbon fuel and the air is not performed, incomplete combustion is generated in a region where the fuel is rich so as to form soot and generate a luminous flame. When unexpected combustion is generated in a combustion chamber in an internal combustion engine, so-called knocking is generated. Detecting generation of such an abnormal reaction and knowing what kind of characteristic the reaction has by measurement and an analysis are essential for making the engine of operating with utilizing the reaction highly efficient and more environmentally friendly.

Conventionally, as a method for detecting reaction abnormality and knowing the characteristic of the reaction, there are an experimental method by human perception, a method by pressure measurement and a pressure analysis of the reaction region, a method by measurement and an analysis of sound or vibration of a reaction chamber, a method of measuring exhaust and the like from the reaction region and analyzing a component thereof and the like. However, since these methods are sensory or indirect methods, reproducibility of detection is not enough and detailed information on the reaction cannot be obtained.

Therefore, there are various proposed techniques such as a technique detecting the generation of the reaction abnormality by directly and optically measuring the reaction region, and a technique obtaining information on a state of the reaction and the like by analyzing light in the region where the reaction is generated. For example, Patent Literature 1 discloses a method comprising: installing an optical sensor in a combustion chamber in correspondence to each self-emitting light of a flame, calculating an air-fuel ratio from a ratio of emission intensity detected by the optical sensor, and diagnosing combustion based on this air-fuel ratio. Alternatively, like a combustion diagnosing method described in Non-patent Literature 2, there is a method comprising: inserting an optical fiber into a combustion chamber, detecting light in the combustion chamber via the optical fiber, and detecting combustion abnormality such as knocking by intensity of the light.

The present inventors propose an optical measurement apparatus described in Patent Literature 2. This optical measurement apparatus is to measure light generated by physical and chemical reactions in a local place in a combustion chamber with using a plug having an optical element forming a reflecting optical system, detect and analyze physical and chemical reaction regions and local physical and chemical reaction characteristics.

[Patent Literature 1] Japanese Patent Laid-Open No. 2005-226893

[Patent Literature 2] Japanese Patent Laid-Open No. 2006-292524

[Non-patent Literature 1] AVL Visiolution Catalog (AVL Japan)

DISCLOSURE OF THE INVENTION

Problems to be Solved by the Invention

In a technique described in Patent Literature 1, the air-fuel ratio is calculated from the ratio of the emission intensity and the combustion is diagnosed by the air-fuel ratio. However, in the case where the soot is formed and the luminous flame is generated in the reaction region due to incomplete combustion, it is not possible to accurately measure the intensity of the self-emitting light. Therefore, it is impossible to calculate the air-fuel ratio. Consequently, with the technique described in Patent Literature 1, such an abnormal reaction cannot be detected.

In a technique described in Non-patent Literature 1, the combustion abnormality is detected by the intensity of the light in the combustion chamber. However, in the case where a focusing performance of the optical fiber is deteriorated by an influence of heat in the reaction region, pressure, a chemical substance in an atmosphere or the like, or by soot adhering to the optical fiber, it is not possible to accurately measure the intensity of the light. Moreover, it is impossible to properly detect the combustion abnormality from an inaccurate measurement value. Therefore, with the technique described in Non-patent Literature 1, it is possible neither to properly calculate the air-fuel ratio nor to ensure the reproducibility of the detection of the abnormal reaction. A problem of the reproducibility of the detection caused by such a light receiving state may occur in techniques described in the above literatures.

In the techniques described in Patent Literature 1 and Non-patent Literature 1, since the light from every direction towards the optical sensor or the optical fiber is detected, spatial resolution is bad. Therefore, even when the abnormal reaction is detected, it is extremely difficult to identify, which position in the reaction region where the abnormal reaction is generated, or which spatial distribution the abnormal reaction takes.

In technique described in Patent Literature 1, a reaction region where the combustion is continuously performed such as a combustor of a gas turbine engine is targeted. The combustion diagnosing apparatus obtains one value which is a ratio of self-emission intensity serving as an arithmetic result from the light which is guided by the optical fiber connected to the combustor. However, with such a method, it is difficult to accurately and precisely analyze the reaction generated in the reaction region.

For example, in the case where the reaction region is a displacement internal combustion engine of a spark ignition type such as a typical engine for an automobile, or in the case where the reaction region is an internal combustion engine of a laser ignition type, discharge or plasma induced by laser light largely influences over later ignition and flame propagation. In addition, in order to obtain information on a state in a cylinder, spectroscopy is performed on light of discharge plasma separately from the ignition or plasma induced with using laser (such as Spark Induced Breakdown Spectroscopy (SIBS) or Laser Induced Breakdown Spectroscopy (LIBS)). However, the spectrum of this light emitted from this plasma is largely different from the spectrum of the light from the flame. In the technique described in Patent Literature 1, it is not possible to judge whether or not the light received by the optical sensor is from the discharge and the laser or the flame.

For example, in the case where the reaction region is the displacement internal combustion engine of the spark ignition type such as the typical engine for the automobile, a flame zone is formed after the ignition and this flame zone is developed in the cylinder so as to achieve the flame propagation. In such a case, a light generation position is changed over time. In the technique described in Patent Literature 1, it is not possible to identify a position where the combustion abnormality or the like is generated.

Further, the typical engine for the automobile is provided with a plurality of cylinders. The flames generated in these cylinders determine performance of the internal combustion engine. In order to obtain the information on the cylinders by the technique described in Patent Literature 1, since at least the same number of a functional portion for spectroscopy, photoelectric conversion, amplification and arithmetic processing as the number of the cylinders has to be provided, the apparatus is unavoidably large-sized.

The present invention is proposed in consideration to the above situation in order to provide a reaction analysis apparatus capable of detecting whether or not a reaction region is in an abnormal reaction state precisely with high reproducibility, a measurement system and a recording medium in which a program for forming the reaction analysis apparatus is recorded.

The present invention is to provide a reaction analysis apparatus capable of executing proper analysis processing in accordance with a state of the reaction region and efficiently analyzing a characteristic of a fuel region, a measurement system and a recording medium in which a program for forming the reaction analysis apparatus is recorded.

The present invention is to provide a reaction analysis apparatus capable of detecting whether or not a reaction region is in an abnormal state with high spatial resolution, a measurement system and a recording medium in which a program for forming the reaction analysis apparatus is recorded.

Means for Solving the Problems

A reaction analysis apparatus according to the present invention comprises obtaining means for obtaining an intensity value of a first wavelength component and an intensity value of a second wavelength component from a measurement result of light emitted from a reaction region by a spectrometer, relative intensity calculating means for calculating relative intensity of the first wavelength component relative to the second wavelength component from the intensity value of the first wavelength component and the intensity value of the second wavelength component obtained by the obtaining means, determining means for determining whether or not the relative intensity calculated by the relative intensity calculating means is a value within a predetermined range, and notifying means for notifying that a state of the reaction region is a predetermined state in response to the determination that the relative intensity is the value within the predetermined range by the determining means.

According to the above configuration, among the measurement result of the light emitted from the reaction region by the predetermined spectrometer, when the relative intensity of the first wavelength component relative to the second wavelength component is within the predetermined value, it is notified that the reaction region is in the predetermined state. In comparison to the intensity value of the first wavelength component or the second wavelength component, this relative intensity is less changed by an influence of an error caused depending on an optical system state at the time of receiving the light emitted from the reaction region and performing spectrometry. Therefore, based on the measurement result of the reaction region by the spectrometer, it is possible to properly detect and notify that the reaction region is in the predetermined state with high reproducibility without being largely influenced by a measurement situation.

Preferably, the obtaining means obtains an intensity value of a wavelength component substantially corresponding to wavelength of light emitted from $C_2^*$ as the intensity value of the first wavelength component, and an intensity value of a wavelength component substantially corresponding to wavelength of light emitted from at least one radical selected from a group consisting of $CH^*$, $CN^*$ and $OH^*$ as the intensity value of the second wavelength component from a measurement result of light emitted from a reaction region of hydrocarbon by the predetermined spectrometer.

According to the above configuration, based on the measurement result of the reaction region of hydrocarbon by the spectrometer, it is possible to properly detect and notify that the reaction region of hydrocarbon is in the predetermined state with high reproducibility.

Preferably, the notifying means notifies that soot is generated in the reaction region in response to the determination that the relative intensity is the value within the predetermined range by the determining means.

According to the above configuration, based on the measurement result of the reaction region by the spectrometer, it is possible to properly detect and notify that the soot is generated in the reaction region with high reproducibility.

In the reaction analysis apparatus according to the present invention, preferably, the obtaining means obtains an intensity value of a third wavelength component and an intensity value of a fourth wavelength component from the measurement result of the light emitted from the reaction region by the spectrometer, the relative intensity calculating means calculates relative intensity of the third wavelength component relative to the fourth wavelength component from the intensity value of the third wavelength component and the intensity value of the fourth wavelength component obtained by the obtaining means, and when the notifying means notifies that the soot is generated in the reaction region in response to the determination that the relative intensity is the value within the predetermined range by the determining means, calculating means calculates a temperature of the soot generated in the reaction region based on the intensity value of the third wavelength component and the intensity value of the fourth wavelength component.

According to the above configuration, the temperature of the soot is calculated from the measurement result when it is notified that the soot is generated in the reaction region. Since the temperature of the soot can be calculated from the measurement result capable of calculating the temperature of the soot, it is possible to efficiently generate information on the temperature of the soot.

The reaction analysis apparatus according to the present invention may be provided with concentration calculating means for calculating a concentration of the soot generated in the reaction region based on the intensity value of the third wavelength component, the intensity value of the fourth wavelength component and the temperature of the soot when the notifying means notifies that the soot is generated in the reaction region.

According to the above configuration, the concentration of the soot is calculated from the measurement result when it is notified that the soot is generated in the reaction region. Since the concentration of the soot can be calculated from the measurement result capable of calculating the concentration of the soot, it is possible to efficiently generate information on the concentration of the soot.

Further preferably, the notifying means notifies that a reaction of emitting light of a continuous spectral pattern is being developed in the reaction region in response to the determination that the relative intensity is the value within the predetermined range by the determining means.

According to the above configuration, based on the measurement result of the reaction region by the spectrometer, it is possible to properly detect and notify that the reaction of emitting the light of the continuous spectral pattern is being developed in the reaction region with high reproducibility.

The notifying means may notify that a luminous flame is generated in the reaction region in response to the determination that the relative intensity is the value within the predetermined range by the determining means.

According to the above configuration, based on the measurement result of the reaction region by the spectrometer, it is possible to properly detect and notify that the reaction region is in a state where the luminous flame is generated with high reproducibility.

The notifying means may notify that incomplete combustion is generated in the reaction region in response to the determination that the relative intensity is the value within the predetermined range by the determining means.

According to the above configuration, based on the measurement result of the reaction region by the spectrometer it is possible to properly detect and notify that the reaction region is in an incomplete combustion state with high reproducibility.

The notifying means may notify that premixing failure of fuel and an oxidant is generated in the reaction region in response to the determination that the relative intensity is the value within the predetermined range by the determining means.

According to the above configuration, based on the measurement result of the reaction region by the spectrometer, it is possible to properly detect and notify that the premixing of the fuel and the oxidant is in an insufficient state notifying that the state of the reaction region is in the predetermined state with high reproducibility.

The notifying means may notify that the state of the reaction region is a predetermined state of a plasma reaction in response to the determination that the relative intensity is the value within the predetermined range by the determining means.

The notifying means may notify that the reaction region is in an initial state of a laser-induced breakdown reaction in response to the determination that the relative intensity is the value within the predetermined range by the determining means.

According to the above configuration, based on the measurement result of a predetermined laser-induced breakdown reaction region by the spectrometer, it is possible to properly detect and notify that the reaction region is in the initial state of the laser-induced breakdown reaction with high reproducibility.

This reaction analysis apparatus may have calculating means for calculating an air excess ratio of the reaction region based on the measurement result by the spectrometer when the determining means determines that the relative intensity is not the value within the predetermined range.

According to the above configuration, when the reaction of emitting the light of the continuous spectral pattern is not developed, an air-fuel ratio is calculated from the measurement result. Therefore, it is possible to avoid calculating the air excess ratio from the measurement result of the light of the continuous spectral pattern with which the peak cannot be properly detected so as to efficiently calculate the air excess ratio.

Preferably, the reaction analysis apparatus further has selecting means for selecting a wavelength range from a first wavelength range and a second wavelength range in accordance with a result of the determination by the determining means, and peak analyzing means for generating predetermined information on a characteristic of the reaction region based on a characteristic quantity of a peak emerging within the wavelength range selected by the selecting means among the measurement result after executing the determination by the determining means.

According to the above configuration, the peak analyzing means generates the predetermined information on the characteristic of the reaction region based on the characteristic quantity of the peak within the wavelength range selected in accordance with the result of the determination by the determining means. That is, the peak analyzing means generates the predetermined information on the characteristic of the reaction region based on the information obtained from the wavelength range selected in accordance with the state of the reaction region. Therefore, it is possible to efficiently provide the information on the characteristic of the reaction region in accordance with the state of the reaction region.

Preferably, the peak analyzing means determines whether or not knocking is generated based on emerging timing of the peak emerging at fifth wavelength and sixth wavelength within the wavelength range selected by the selecting means among the measurement result after executing the determination by the determining means, and generates information showing a result of the determination.

According to the above configuration, it is possible to determine whether or not the knocking is generated by efficient processing in accordance with the state of the reaction region. Since it is determined whether or not the knocking is generated by the light emitted from the reaction region, information on a generation position of the knocking is more easily obtained than determination of the knocking by vibration or pressure. Information on emerging timing of the peak is less changed by an influence of an error caused depending on a measurement system state of the light rather than strength of the light emitted in the reaction region and the intensity value of the peak. Therefore, based on the measurement result by the spectrometer, it is possible to properly determine the generation of the knocking with high reproducibility without being largely influenced by the measurement situation.

Preferably, the peak analyzing means determines whether or not knocking is generated based on a temporal change of intensity at the peak emerging at fifth wavelength and sixth wavelength within the wavelength range selected by the selecting means among the measurement result after executing the determination by the determining means, and generates information showing a result of the determination.

According to the above configuration, it is possible to determine whether or not the knocking is generated by efficient processing in accordance with the state of the reaction region. Since it is determined whether or not the knocking is generated by the light emitted from the reaction region, information on a generation position of the knocking is more easily obtained than determination of the knocking by vibration or pressure. Since a time period when the peak emerges is short, there is less influence of the error caused depending on the measurement system state of the light. Therefore, based on the measurement result by the spectrometer, it is possible to properly determine the generation of the knocking with high reproducibility without being largely influenced by the measurement situation.

Preferably, the peak analyzing means calculates propagation speed of the reaction in the reaction region based on the characteristic quantity of the peak emerging within the wavelength range selected by the selecting means among the measurement result after executing the determination by the determining means.

According to the above configuration, it is possible to efficiently provide information on the propagation speed of the reaction in the reaction region in accordance with the state of the reaction region.

Preferably, the peak analyzing means calculates thickness of a reaction zone in the reaction region based on the characteristic quantity of the peak emerging within the wavelength range selected by the selecting means among the measurement result after executing the determination by the determining means.

According to the above configuration, it is possible to efficiently provide information on the thickness of the reaction zone in the reaction region in accordance with the state of the reaction region.

Preferably, the peak analyzing means calculates a temperature analysis of the reaction region based on the characteristic quantity of the peak emerging within the wavelength range selected by the selecting means among the measurement result after executing the determination by the determining means.

According to the above configuration, it is possible to efficiently provide information on the temperature of the reaction region in accordance with the state of the reaction region.

Preferably, the peak analyzing means analyzes a component of the reaction region based on the characteristic quantity of the peak emerging within the wavelength range selected by the selecting means among the measurement result after executing the determination by the determining means.

According to the above configuration, it is possible to efficiently provide information on the component of the reaction region in accordance with the state of the reaction region.

The determination of the relative intensity between the first wavelength component and the second wavelength component involves obtaining a pair of two wavelength components out of preliminarily fixed three or more wavelength components, calculating relative intensity for the pair, and determining whether or not relative intensity forming a group consisting of the calculated relative intensities satisfies a predetermined condition.

A reaction analysis apparatus according to the present invention includes an embodiment in which information on pressure is generated and outputted based on width of the peak emerging at two or more wavelengths within the wavelength range selected by the selecting means.

In this reaction analysis apparatus, the information on the pressure is information on partial pressure of the reaction region.

A program is recorded in a recording medium according to the present invention, and the program is executed by a computer for operating the computer as the reaction analysis apparatus mentioned above.

Since the computer reads out and executes the program recorded on this recording medium, it is possible to realize an effect of the above reaction analysis apparatus by the computer.

A measurement system according to the present invention has any of the reaction analysis apparatus according to the present invention, an optical element for, when light is incident from an object point, focusing the light on an image point, and spectrometry means for performing spectrometry on the light focused on the image point by the optical element and outputting a result of the spectrometry as a signal, in which the reaction analysis apparatus receives the signal outputted by the spectrometry means.

According to the above configuration, the light generated on the object point is focused on the image point by the optical element, the spectrometry means performs spectrometry on the focused light, and the above reaction analysis apparatus receives the result thereof. Therefore, based on the light generated by the reaction occurring in a local place including the object point, it is possible to properly notify that the local place is in a predetermined state with high reproducibility without being largely influenced by the state of the optical element.

Preferably, the optical element is integrally formed so as to have a first surface and a second surface in order from the side of the object point, the first surface and the second surface have a first region and a second region respectively, the first region of the first surface is a concave permeable surface, the first region of the second surface is a concave reflecting surface, the second region of the first surface is a reflecting surface, and the light incident from the object point is reflected on the first region of the second surface and the second region of the first surface so as to focus the light on the image point.

In a reflective optical element, since a surface which contributes to image formation is the reflecting surface, chromatic aberration is not generated and there is a favorable image formation property. Therefore, based on the light generated by the reaction occurring in the local place including the object point, it is possible to properly notify that the local place is in the predetermined state with high reproducibility and high spatial resolution without being largely influenced by the state of the optical element.

A measurement system according to the present invention has a time division function of a measurement result (a repeated measurement function and a multi-point measurement unification function), spectrometric means (or a functional portion disposed between the spectrometric means and the reaction analysis apparatus) divides a signal of a result of spectrometry in time direction based on periodicity of the signal, and the reaction analysis apparatus has a time division function of the measurement result for executing an analysis on each piece of signal divided in time direction as a result of spectrometry.

In this measurement system, a plurality of optical elements may be provided, and light focused by a plurality of the optical elements may be focused to be single light so as to perform spectrometry.

Further in this measurement system, the spectrometric means may divide each piece of signal divided in time direction into a spectrometry result for each optical element based on preliminarily fixed information (in order of receiving the light).

The measurement system according to the present invention can be provided with an exceptional processing function in the case where LIBS or SIBS is performed. That is, in this measurement system, the spectrometry means can perform not processing of the reaction analysis apparatus but exceptional processing to transfer to other processing, on a spectrometry result within a predetermined period since intensity of a wavelength component corresponding to wavelength of a laser is high in the case where LIBS is performed, and a spectrometry result within a predetermined period since a current value flowing to a plug is high in the case where SIBS or light of spark discharge is measured.

That is, this measurement system comprises obtaining means for obtaining an intensity value of a first wavelength component and an intensity value of a second wavelength component from a measurement result of light emitted from a reaction region by a spectrometer, relative intensity calculating means for calculating relative intensity of the first wavelength component relative to the second wavelength component from the intensity value of the first wavelength component and the intensity value of the second wavelength component obtained by the obtaining means, determining means for determining distinction between thermal excitation emission, chemiluminescence (including a flame and plasma) and Bremsstrahlung by a range of the relative intensity calculated by the relative intensity calculating means, and notifying means for notifying that a state of the reaction region is a predetermined state in response to determination that the relative intensity is the value within the predetermined range by the determining means.

In this measurement system, an analysis of an ion, an analysis of an atom and an analysis of a molecule in the reaction region are performed in order from the measurement result at a time point when a determination result by the determining means is the Bremsstrahlung in accordance with time development of the measurement result.

This measurement system comprises a plurality of analyzing means for performing different processing to each other, to the measurement result by the spectrometry on the light emitted from the reaction region so as to generate predetermined information corresponding to the processing with regard to characteristic of the reaction region respectively, wavelength selecting means for selecting two or more wavelengths from the measurement result, relative intensity calculating means for calculating relative intensity of one wavelength component relative to the other wavelength component with regard to each team consisting of a combination of wavelength of the two or more wavelength, determining means for determining a region where the thermal excitation emission, the chemiluminescence (including a flame and plasma) and the Bremsstrahlung are generated in space of the measurement result formed by three dimensions of the wavelength, the intensity and the time, and range setting means for setting a range where a plurality of the analyzing means perform the processing in accordance with the determination result by the determining means.

Further in this measurement system, the wavelength selecting means selects wavelength of light of the chemiluminescence due to the atom, the molecule or the ion, or arbitrary wavelength within a wavelength band exceeding about 431 nm, and the selected wavelength includes at least one of wavelength selected from a wavelength band not more than about 431 nm, and at least one of wavelength selected from a wavelength band exceeding about 431 nm.

Further in this measurement system, the processing by a plurality of the analyzing means is processing selected from processing by a two-color method, processing of generating the predetermined information based on a characteristic quantity of a peak generated by self emitting light, or processing of generating the predetermined information based on a characteristic quantity of a peak of light generated by breakdown due to an input of high energy (LIBS, SIBS).

Further in this measurement system, the range setting means performs processing in order of processing of generating the predetermined information for the ion, processing of generating the predetermined information for the atom, and processing of generating the predetermined information for the molecule, in the processing of generating the predetermined information based on the characteristic quantity of the peak of the light generated by the breakdown due to the input of high energy (LIBS, SIBS) from the region where the Bremsstrahlung is generated.

In the measurement system according to the present invention, in the reaction analysis apparatus, the relative intensity is an angle between a straight line from a position corresponding to the intensity value of the first wavelength component to a position corresponding to the intensity value of the second wavelength component and a wavelength axis on a spectral plane taking the wavelength and the intensity value as axes.

Further in the measurement system according to the present invention, the optical element is integrally formed with at least one energy input means selected from the group of energy input means consisting of a discharge electrode, a laser outputting device and a microwave radiation antenna.

Effect of the Invention

As mentioned above, the reaction analysis apparatus according to the present invention is to notify that the reaction region is in the predetermined state when the relative intensity of the first wavelength component relative to the second wavelength component is within the predetermined value. Therefore, based on the measurement result of the reaction region by the spectrometer, it is possible to properly detect and notify that the reaction region is in the predetermined state with high reproducibility without being largely influenced by the measurement situation.

Based on the measurement result of the reaction region by the spectrometer, it is possible to properly notify that the soot is generated in the reaction region with high reproducibility, and efficiently provide the information on the temperature or the concentration of the soot.

Based on the measurement result of the reaction region by the spectrometer, it is possible to properly detect and notify that the reaction of emitting the light of the continuous spectral pattern is being developed in the reaction region with high reproducibility, and also efficiently calculate the air excess ratio.

It is also possible to properly detect and notify the generation of the luminous flame in the reaction region, the incomplete combustion or the state that the premixing of the fuel and the oxidant is insufficient, or the predetermined state of the plasma reaction, or the initial state of the laser-induced breakdown reaction with high reproducibility.

The peak analyzing means generates the predetermined information on the characteristic of the reaction region based on the information obtained from the wavelength range selected in accordance with the state of the reaction region. Therefore, it is possible to efficiently provide the information on the characteristic of the reaction region in accordance with the state of the reaction region.

It is also possible to determine whether or not the knocking is generated by efficient processing in accordance with the state of the reaction region. Further, based on the measurement result by the spectrometer, it is possible to properly detect the generation of the knocking with high reproducibility without being largely influenced by the measurement situation.

It is also possible to efficiently provide the information on the propagation speed of the reaction in the reaction region, the thickness of the reaction zone, the temperature of the reaction region, and the component of the reaction region in accordance with the state of the reaction region.

In the reaction analysis apparatus according to the present invention, there is the exceptional processing function for the case of performing LIBS, SIBS or the like. Therefore, it is possible to properly and efficiently perform an analysis of the reaction based on the light emitted from the reaction region due to the laser or the discharge.

Further, in the reaction analysis apparatus according to the present invention, the angle between the straight line from the position corresponding to the intensity value of the first wavelength component to the position corresponding to the intensity value of the second wavelength component and the wavelength axis on the spectral plane taking the wavelength and the intensity value as axes is used as the relative intensity. Therefore, calculation thereafter is easily performed.

In the measurement system according to the present invention, the light generated on the object point is focused on the image point by the optical element, the spectrometry means performs spectrometry on the focused light, and the above reaction analysis apparatus receives the result thereof and notifies that the reaction region is in the predetermined state. Therefore, based on the light generated by the reaction occurring in the local place, it is possible to properly detect and notify that the local place is in the predetermined state with high reproducibility without being largely influenced by the state of the optical element.

In the reflective optical element, since the surface which contributes to the image formation is the reflecting surface, the chromatic aberration is not generated and there is a favorable image formation property. Therefore, based on the light generated by the reaction occurring in the local place, it is possible to properly detect and notify that the local place is in the predetermined state with high reproducibility and high spatial resolution without being largely influenced by the state of the optical element.

The measurement system according to the present invention has the time division function of the measurement result (in correspondence to repeated measurement and unification of multi-point measurement). Therefore, it is possible to perform the analysis in which the light in the reaction region where the reaction is periodically developed is divided for each periodic reaction.

In the case where the measurement and the analysis are performed at a plurality of positions on one reaction region where a position of the reaction accompanied by light emission is moved over time, or in the case where the measurement and the analysis are performed on an object in which the reaction is developed connectedly in a plurality of reaction regions such as a multi-cylinder engine, it is possible to perform spectroscopy with a single hardware.

Further, while spectroscopy is performed with a single hardware, it is possible to relate a measurement position, that is, arrangement of a spectroscopic element to results of the measurement and the analysis. Thereby, the processing such as the analysis of a change between cylinders performed with using a plurality of measurement systems can be realized with one system. It is possible to downsize the system by unifying the hardware of spectrometry. It is also possible to reduce the number of parts and decrease a measurement error due to the hardware for performing spectrometry.

The control system of the present invention also includes a control system for controlling a reaction region in a state corresponding to a given input, and the control system is provided with a measurement system, converting means for converting an output from the measurement system into an input value corresponding to the output, and adjusting means for giving the input value to the reaction region.

In this control system according to the present invention, the input value is one or more value selected from the group consisting of a position, a path, an altitude, a posture, a direction, size, volume, an angle, a flow rate, density, linear speed, angular speed, acceleration, mechanical force, stress, fluid pressure, torque, amplitude, frequency, phase, a numerical quantity, a physicochemical variable quantity, a component, a mix ratio, humidity, a temperature, viscosity, a light amount, color, electric charge, voltage, an electric current, magnetic flux density, and a radiation dose.

The present invention also provides a control system for controlling an internal combustion engine to operate in a state corresponding to a given input, wherein the control system is provided with a measurement system, converting means for converting an output by the measurement system into an input value corresponding to the output, and adjusting means for giving the input value to the reaction region.

In the control system according to the present invention, the input value is one or more value selected from the group consisting of an inlet flow, inlet humidity, supply pressure of oxidant, a mix ratio of a component in the oxidant, amount of fuel supply, fuel supply speed, a fuel supply position, a fuel supply direction, fuel supply timing, a fuel grain diameter, a fuel penetration degree, a mixing degree, valve timing, relative time difference for opening and closing between valves, ignition timing, input energy for ignition, swirl strength, tumble strength, strength of disturbance of a working fluid in the vicinity of an ignition plug, the kind of a gauge to be operated, an quantity of the gauge to be operated, arrangement of the gauge to be operated, exhaust recirculation volume, a temperature of exhaust to be re-circulated, pressure of an exhaust pipe, afterburning, a qualitative component of the exhaust, a quantitative component of the exhaust, and vibration of pressure wave.

EXPLANATION OF REFERENCE NUMERALS

Figure 1:
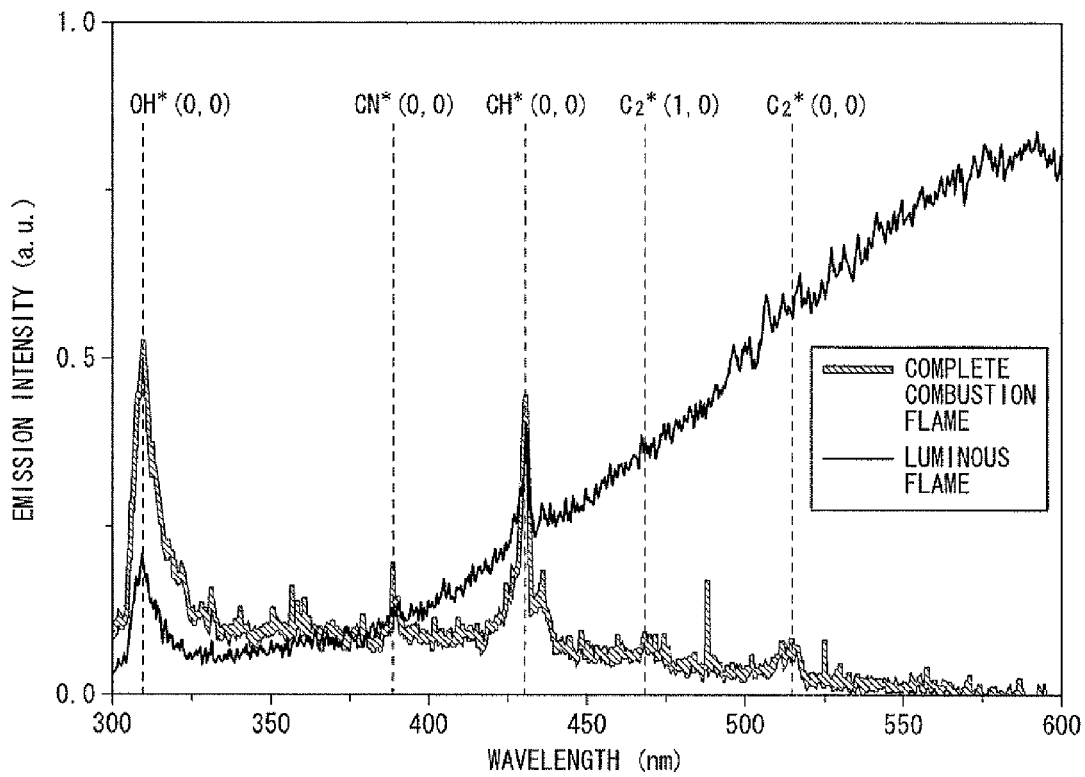
FIG. 1 A graph showing two kinds of spectra for illustrating a concept of one embodiment of the present invention.

104: Optical element
106: Optical fiber cable
108A to 108N: Optical fiber
110A to 110N: Spectrometer
114: Reaction analysis apparatus
140: First surface
140A, 142: First region
140B, 142B: Second region
142: Second surface
144, 146: Reflecting film
148: Protection film
150: Stray light aperture
200: Computer system
300: Signal conversion portion
302: Spectroscopic data memory
304: Spectral pattern determination portion
306: Processing selection portion
308: Continuous pattern analysis portion
310: Peak analysis portion
312: Analysis result memory
314: User interface
316: Output portion
330: First intensity value obtaining portion
332: Second intensity value obtaining portion
334: Relative intensity calculating portion
336: Reference value memory
338: Determination portion
350: Data reading portion
352: Temperature calculating portion
354: Concentration calculating portion
370: Peak detection portion
372: Peak characteristic quantity extracting portion
374: Statistical processing portion
376: Calibration information memory
378: Characteristic quantity analysis portion
104P to S: Optical element
106P to S: Optical fiber cable
108nP to S: Optical fiber
700, 800, 900: Measurement system
702: Spectrometer
708, 804: Signal splitter
802: Optical fiber bundle
902: Processing selector

BEST MODES FOR CARRYING OUT THE INVENTION

Hereinafter, embodiments of the present invention will be described with reference to the drawings. It should be noted that in the drawings used in the following description, the same reference numerals are given to the same parts. The same parts have same names and functions.

[Concept of the Present Invention]

Firstly, a concept of the present invention will be described taking a flame as an example below. When fuel and an oxidant are appropriately mixed, the fuel is completely combusted. In this state, the fuel is all ionized and excited so as to be a radical. At that time, light is emitted from the radical in the flame. Meanwhile, when mixing of the fuel and the oxidant is inappropriate, incomplete combustion is generated in a part where the fuel is rich. In this state, the fuel does not completely become plasma but a part thereof becomes minute particles so as to be diffused. The minute particles are soot and smoke. The soot smoke is heated by the flame so as to emit strong light due to blackbody radiation. A so-called luminous flame is formed by this light.

With regard to a flame and a luminous flame in the case where methane gas is completely combusted in the air, FIG. 1 shows spectra in a wavelength band in the vicinity of 300 nm to 550 nm of the light emitted from the flames in contrast with each other. With reference to FIG. 1, light having a special wavelength component in accordance with the kind of radical is emitted from the radical. Therefore, in the spectrum emitted from the flame of the complete combustion, a spectral pattern having several sharp peaks is recognized. Meanwhile, in the luminous flame, a component of the light emitted by the blackbody radiation is detected in addition to a component of the light emitted from the radical. In the blackbody radiation, the light having a wide wavelength band component is emitted unlike the light emitted from the radical. Therefore, in the spectrum of the light emitted from the luminous flame, a continuous spectral pattern is recognized particularly in a long wavelength band.

In such a spectral pattern, intensity of light emitted from $C_2^*$ cannot be determined. Therefore, from a ratio between intensity of a component at wavelength of about 473 nm or about 516 nm corresponding to the light emitted from $C_2^*$ and intensity of a component at wavelength of about 431 nm corresponding to light emitted from $CH^*$, none of an air excess ratio, an equivalent ratio and an air-fuel ratio can be calculated. However, the ratio between the intensity of the component at the wavelength of about 473 nm or about 516 nm and the intensity of the component at the wavelength of about 431 nm is a largely different value between the spectrum of the light emitted from the flame of the complete combustion and the spectrum of the light emitted from the luminous flame. Even in such a spectral pattern, in a wavelength band of the wavelength of about 431 nm or less corresponding to the light emitted from CH*, the peak can be recognized in the wavelength corresponding to the light emitted from the radical.

In the present embodiment, such a difference in the spectral patterns is determined based on a relative value between intensities of two wavelength components which are measured at the same time (hereinafter, referred to as the "relative intensity") from information on the spectra of the flame. Thereby, generation of the luminous flame or soot, a state of fuel premixing failure or the like is detected. In the present embodiment, in a wavelength band where the peak of the intensity on the spectrum due to the light emitted from the radical can be detected, analysis processing including detection of occurrence of knocking is executed based on characteristics, such as timing of the peak, the wavelength, the intensity, spectral line width and line shape, is performed, and information on a reaction region is obtained.

[Entire Configuration]

Figure 2:
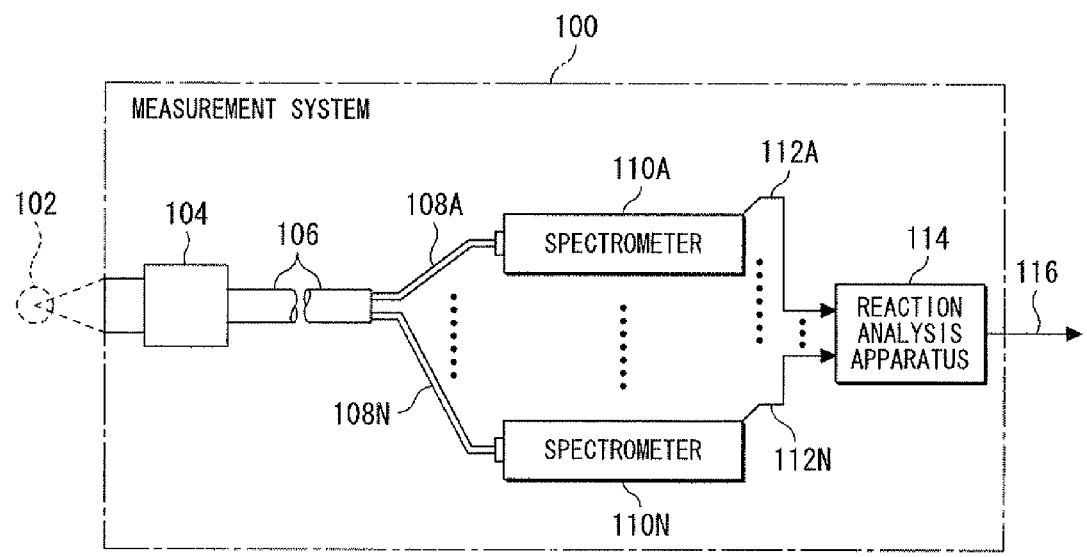
FIG. 2 A block diagram showing an entire configuration of a measurement system according to one embodiment of the present invention.

FIG. 2 shows a schematic configuration of a measurement system according to the present embodiment. With reference to FIG. 2, a measurement system 100 has: an optical element 104 for focusing light emitted from the reaction region or from a measurement region 102 nearby; an optical fiber cable 106 provided with a plurality of optical fibers 108A to 108N with one ends arranged at a focusing position of the optical element 114 for the light emitted from the measurement region 102, for emitting the light incident to the one ends from the other ends; spectrometers 110A to 110N connected to the other ends of the optical fibers 108A to 108N respectively, for performing spectroscopy for the light emitted from the other ends, and outputting measurement signals 112A to 112N serving as electric signals in accordance with intensities of components after spectroscopy; and a reaction analysis apparatus 114 for receiving the measurement signals 112A to 112N, executing signal processing to the measurement signals 112A to 112N so as to detect generation of the luminous flame in the measurement region 102, performing an analysis on an object to be measured which is in the measurement region 102, physical and chemical states thereof and the like based on a detection result thereof and the measurement signals 112A and 112N, and outputting an analysis result 108 thereof.

[Optical Element]

Figure 3:
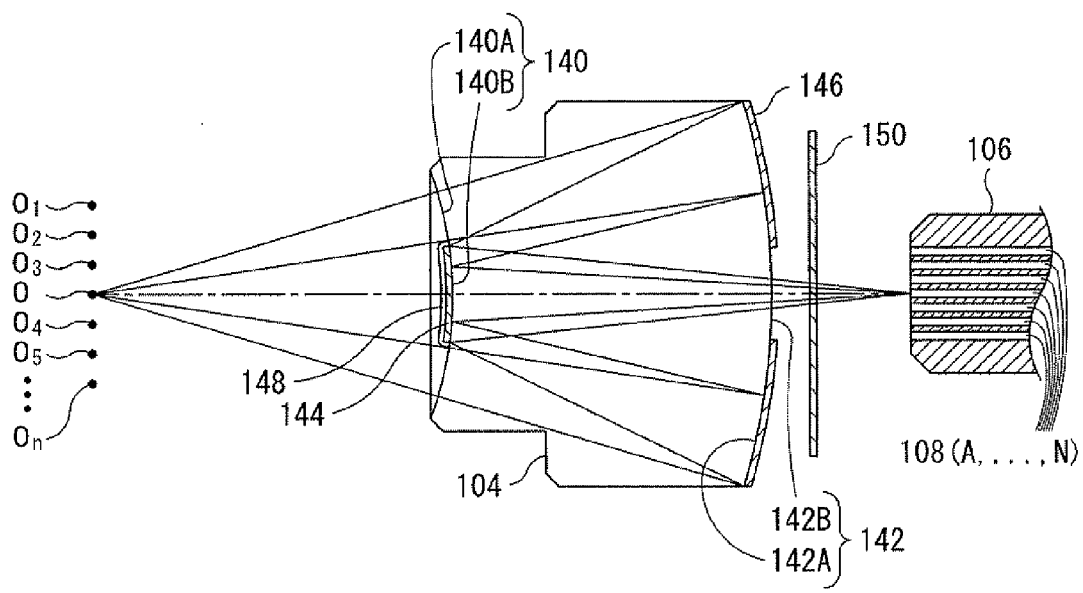
FIG. 3 A sectional view showing a configuration of an optical element in the measurement system.

FIG. 3 shows a sectional view of the optical element 104 according to the present embodiment. With reference to FIG. 3, the optical element 104 is an integral optical element having a first surface 140 and a second surface 142. There is a translucent and uniform medium between the first surface 140 and the second surface 142. Specifically, the medium is a so-called optical glass or quartz or the like.

The first surface 140 and the second surface 142 have first regions 140A and 142A on the outer peripheral side and second regions 140B and 142B in center parts respectively. The first region 140A of the first surface 140 is a spherical permeable surface taking a predetermined point O as a curvature center. A first reflecting film 144 made of a reflecting material such as a metal material (aluminum, for example) is formed and adhered to the second region 140B of the first surface 140. Therefore, the second region 140B of the first surface 140 is a reflecting surface of incident light from the medium side. Further, a protection film 148 for protecting the reflecting film 134 from the object to be measured is formed on the side of the measurement position 102 of the reflecting film 144. A second reflecting film 146 made of the same reflecting material as the first reflecting film 144 is formed and adhered to the first region 142A of the second surface 142. That is, the first region 142A of the second surface 142 is a concave reflecting surface of the light from the medium side. The second region 142B of the second surface 142 is a spherical permeable surface taking a point I as a curvature center. Hereinafter, the point O is referred to as the "object point" and the point I is referred to as the "image point".

The light from the object point O is incident on the first region 140A of the first surface 140, going through the medium between the first surface 140 and the second surface 142, and reflected on the first region 142A of the second surface 142. The light reflected on the first region 142A of the second surface 142 is reflected on the second region 140B of the first surface 140, emitted through the second region 142B of the second surface 142, and focused on the image point I via a stray light aperture 150. Light from points $O_1$, $O_2$, $O_3$, $O_4$, $O_5$ to $O_n$, on the side of the object point O is also focused on an image formation surface on the side of the image point I by the optical element 104. Therefore, in this optical element 104, since only the reflecting surface is a surface which contributes to optical paths of the light from the object points $O_1$, $O_2$, $O_3$, $O_4$, $O_5$, and $O_n$, chromatic aberration is not generated.

An end surface on the incident side of the optical fiber cable 106 is arranged so that incident end surfaces of the optical fibers 108A to 108N are arranged towards the second region 140B of the first surface 140 on the image formation surface of the optical element 114 including the image point I. Therefore, the light generated in the object points $O_1$, $O_2$, $O_3$, $O_4$, $O_5$ to $O_n$ is focused by the fibers 108A to 108N arranged at positions on the image formation surface corresponding to the object points by the optical element 104. The focused light is incident on the fibers 108A to 108N and emitted from end surfaces on the side of the spectrometers 110A to 110N via the optical fibers 108A to 108N.

[Spectrometer]

Figure 4:
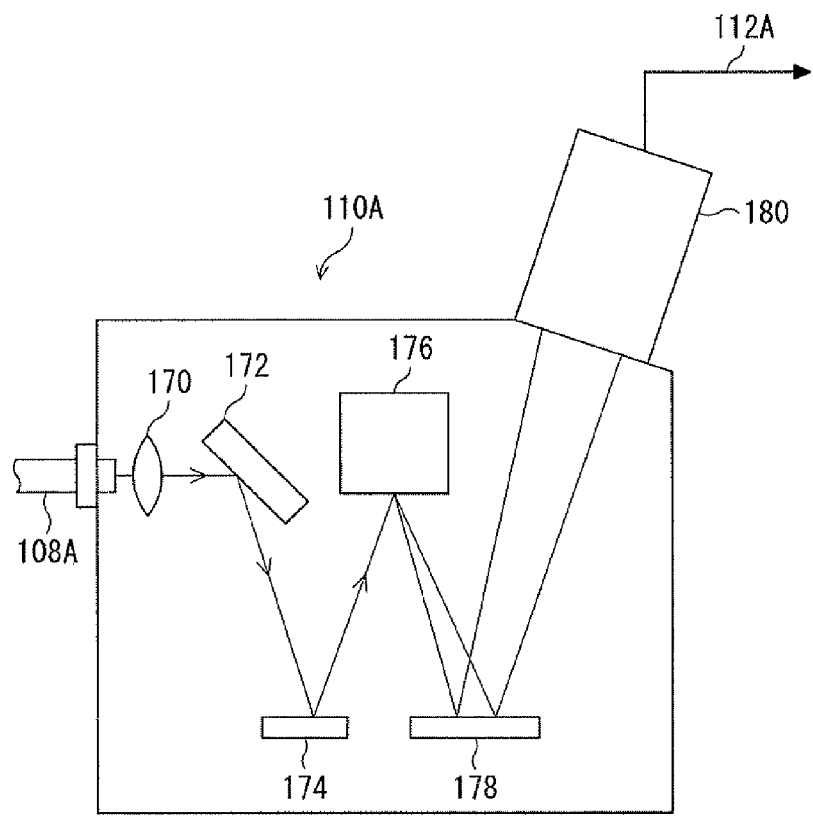
FIG. 4 A side view showing a configuration of a spectrometer in the measurement system.

The spectrometers 110A to 110N shown in FIG. 1 have the same configuration as each other except that the optical fibers to be connected are different. FIG. 4 shows a side view of the spectrometer 110A as a representative. With reference to FIG. 4, the spectrometer 110A has: a collimator 170 arranged on an optical axis of the light emitted from the optical fiber 108A, for converting the light emitted from the optical fiber 108A into parallel light; a first mirror 172 arranged on an optical axis of the parallel light converted by the collimator 170; a second mirror 174 arranged on an optical axis of reflected light of the parallel light emitted via the collimator 170 and reflected by the first mirror 172; a spectroscopic element 176 arranged on an optical axis of reflected light of the parallel light emitted via the collimator 170 and reflected by the second mirror 174, for performing spectroscopy on and emitting the light reflected by the second mirror 174; a third mirror 178 arranged on an optical path of spectral light after spectroscopy by the spectroscopic element 176; and a light detector 180 arranged on an optical path of the spectral light reflected by the third mirror 178, for sequentially performing photoelectric conversion on the incident spectral light and outputting a time-series electric signal obtained as a result thereof as the measurement signal 112A.

Specifically, the spectroscopic element 176 is a diffraction grating, a prism or the like. Specifically, the light detector 180 is a CCD image sensor or the like where a number of charge-coupled devices (CCD) or the like are arranged in matrix. The mirrors 172, 174 and 178 are arranged so as to make predetermined angles relative to the incident light, so that the light is not congested in a process from the incidence of the light generated from the plasma, spectroscopy by the spectroscopic element 176, until receipt by the light detector 180.

Spectroscopy is performed on the light reaching to the spectroscopic element 176 by the spectroscopic element 176 so as to form the spectral light, and the light reaches the light detector 180 via the mirror 178. Therefore, a light receiving position for each component of the spectral light on the light detector 180 is different according to wavelength thereof. Meanwhile, the light detector 180 successively performs the photoelectric conversion on the light received at each light receiving position, and outputs the measurement signal 112A including information on the light receiving position at that time point and intensity of the light at the light receiving position. Therefore, the measurement signal 112A outputted by the light detector 180 includes the information on the intensity of each wavelength component contained in the light emitted from the object point $O_1$ at each time point.

[Realization and Action of Signal Processing Portion by Computer]

Figure 5:
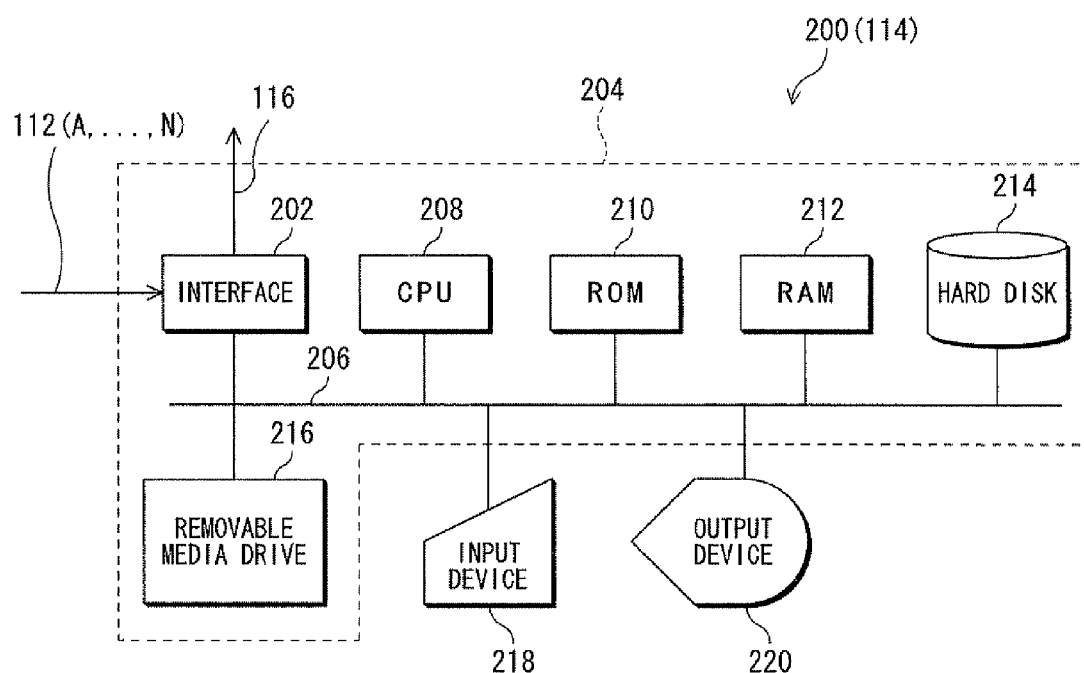
FIG. 5 A block diagram showing an internal configuration of a computer system operated as a reaction analysis apparatus in the measurement system.

Functions of the reaction analysis apparatus 114 of the present embodiment can be realized by a computer hardware, a program executed by the computer hardware, and data stored in the computer hardware. FIG. 5 shows a configuration of a computer system 200 for realizing the functions of this reaction analysis apparatus 114.

With reference to FIG. 5, this computer system 200 has: a computer 204 having an interface 202 for an input of the measurement signals 112A to 112N and an output of an analysis result 116; an input device 218 connected to the computer 204 such as a keyboard; and an output device 220 connected to the computer 204 such as a display device.

The computer 204 has: a bus 206 connected to the interface 202; and a central processing unit (CPU) 208 in addition to the interface 202. The computer 204 further has: a read only memory (ROM) 210 for storing a boot-up program and the like; a random access memory (RAM) 212 for storing a program instruction, a system program, working data and the like; a hard disk 214; and a removable media drive 216. The CPU 208, the ROM 210, the RAM 212, the hard disk 214 and the removable media drive 216 are all connected to the bus 186. Although not shown here, the computer 204 may be further provided with a network adapter board for connection to a local area network (LAN).

A program for operating the computer system 200 as the reaction analysis apparatus 114 is stored in a removable media inserted in the removable media drive 216. A stored content thereof is transferred to the hard disk 214. The program may be transmitted to the computer 204 through a network (not shown) and stored in the hard disk 214. The program is loaded onto the RAM 212 at the time of executing the program. It should be noted that the program may be loaded onto the RAM 212 not via the hard disk 214 but directly from the removable media or the network.

This program includes a plurality of instructions by which the computer 204 executes actions as the reaction analysis apparatus 114. Several fundamental functions required for the instructions to execute the actions are provided by an operating system (OS) installed in the computer 204 and operated on the computer 204, a program of a third party or a module of various toolkits. Therefore, this program does not necessarily include all the functions required to realize the actions of the reaction analysis apparatus 114. This program only needs to include instructions to execute the functions of the reaction analysis apparatus 114 by calling a proper function, a tool and the like by a method which is controlled so as to obtain a desired result. Since actions of the computer system 204 itself is already known, description thereof will not be repeated.

[Functional Configuration]

Figure 6:
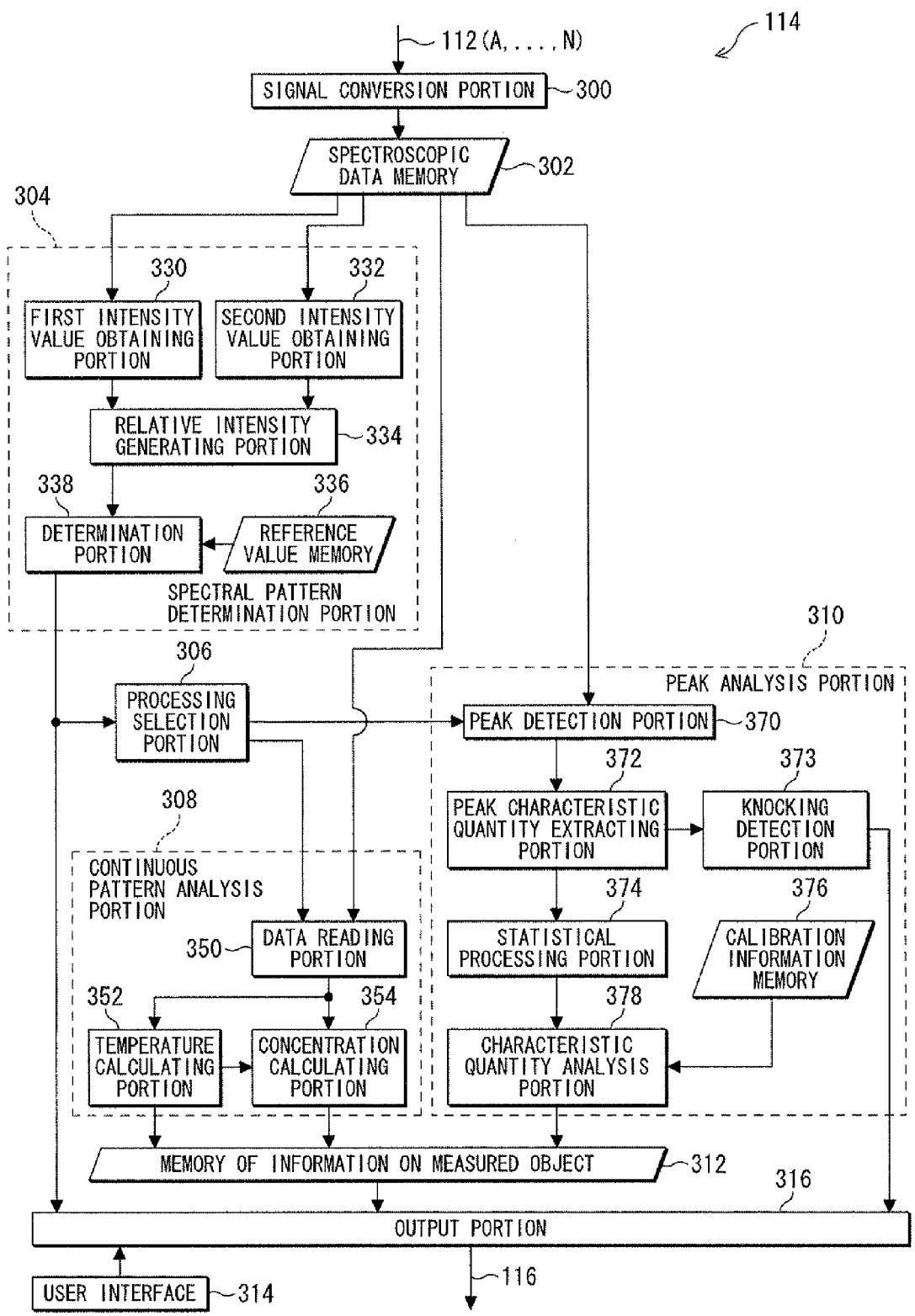
FIG. 6 A block diagram showing a functional configuration of the reaction analysis apparatus in the measurement system.

FIG. 6 shows a functional configuration of the reaction analysis apparatus 114 as a block diagram. With reference to FIG. 6, the reaction analysis apparatus 114 has: a signal conversion portion 300 for receiving and converting the measurement signals 112A to 112N into time-series data showing the intensities of each wavelength components of the light emitted from each positions in the measurement region 102 at each time points (hereinafter, referred to as the "spectroscopic data"); and a spectroscopic data memory 302 for retaining the spectroscopic data generated by the signal conversion portion 300.

The reaction analysis apparatus 114 further has: a spectral pattern determination portion 304 for determining whether each spectrum at a time point and at a position is a spectral pattern having peaks over the entire band or a spectral pattern having a continuous part based on the spectroscopic data; processing selection portion 306 for selecting analysis processing to be executed based on a result of determination by the spectral pattern determination portion 304, and outputting an instruction corresponding to a result of selection; a continuous pattern analysis portion 308 for executing the analysis of the spectroscopic data of the spectrum having the continuous pattern while following the instruction from the processing selection portion 306, and outputting a result thereof; and a peak analysis portion 310 for executing determination of the knocking and the analysis of the reaction region based on the peak on the spectrum on the basis of the spectroscopic data while following the instruction from the processing selection portion 306, and outputting a result thereof.

Specifically, the selection of the processing by the processing selection portion 306 is as follows. That is, with regard to the spectroscopic data at the time point which is determined to have the continuous spectral pattern among the time points on the spectroscopic data, the processing selection portion 306 selects analyses by both the continuous pattern analysis portion 308 and the peak analysis portion 310. Further, a first wavelength range which is not heavily influenced by the continuous spectral pattern is selected as a wavelength range of a peak to be analyzed by the peak analysis portion 310. The first wavelength range is specified as the wavelength range of the peak to be analyzed. With regard to other time points, the analysis only by the peak analysis portion 310 is selected, and further a second wavelength range serving as an entire wavelength range on the spectroscopic data is specified as the wavelength range of the peak to be analyzed by the peak analysis portion 310.

When a cause of generating the continuous spectral pattern is already known, the wavelength range which is not heavily influenced by the continuous spectral pattern can be predicted in accordance with the cause. For example, with regard to the luminous flame as shown in FIG. 1, in a wavelength band of about 431 nm or less corresponding to the light emitted from CH*, there is a minor influence of the luminous flame due to the soot. Therefore, in the present embodiment, information on a wavelength range in the limited case is prepared beforehand, and the processing selection portion 306 retains this and uses this information at the time of selection.

The reaction analysis apparatus 114 further has: an analysis result memory 312 for retaining an analysis result outputted by the continuous pattern analysis portion 308 and the peak analysis portion 310; an user interface 316 for receiving an operation of instructing an output of the analysis result or the like by an user; and an output portion 314 for converting and outputting the result of determination by the spectral pattern determination portion 304 and the result of determination of the knocking by the peak analysis portion 310 into information on a state of the measurement region 102, and reading out and outputting measured object information retained in the analysis result memory 312 based on the operation received by the user interface 316. Specifically, the information outputted by the output portion 314 based on the result of determination by the spectral pattern determination portion 304 is notice of soot generation, notice of fuel pre-mixing failure, generation of the luminous flame or the like.

The spectral pattern determination portion 304 has: a first intensity value obtaining portion 330 for obtaining an intensity value of a first wavelength component (hereinafter, referred to as the first intensity value") used for the determination of the spectral pattern from the retained spectroscopic data; a second intensity value obtaining portion 332 for obtaining an intensity value of a second wavelength component (hereinafter, referred to as the "second intensity value"); a relative intensity calculating portion 334 for calculating relative intensity of the first intensity value relative to the second intensity value; a reference value memory 336 for retaining reference value information on a relationship between the relative intensity and the type of the spectral pattern; and a determination portion 338 for determining whether or not the spectral pattern is continuous by comparing the relative intensity and the reference value information.

A wavelength component whose intensity is largely changed by a difference in the continuous spectral pattern is desirably selected as the first wavelength component. A wavelength component whose intensity is relatively slightly changed by the difference in the continuous spectral pattern is desirably selected as the second wavelength component. For example, in the case where a combustion reaction of hydrocarbon fuel is performed in the measurement region 102 (refer to FIG. 2), a wavelength component in the vicinity of about 473 nm or about 516 nm corresponding to the light emitted from $C_2$* may be selected. As the second wavelength component, for example, in the case where the combustion reaction of the hydrocarbon fuel is performed in the measurement region 102 (refer to FIG. 2), a wavelength component corresponding to the light emitted from CH*, CN* or OH* may be selected.

The continuous pattern analysis portion 308 has: a data reading portion 350 for reading out intensity values of a third wavelength component and a fourth wavelength component required for the analysis from the continuous spectral pattern from the spectroscopic data memory 302 while following the instruction corresponding to the analysis processing of the continuous spectral pattern from the processing selection portion 306; a temperature calculation portion 352 for calculating a temperature of a particle generating the blackbody radiation based on the intensity values of the third and fourth wavelength components read out by the data reading portion 350; and a concentration calculating portion 354 for calculating a concentration of the particle based on the temperature calculated by the temperature calculating portion 352 and the intensity value of the fourth wavelength component. Both the third wavelength component and the fourth wavelength component are desirably a wavelength component out of the second wavelength range. For example, a wavelength component of about 680 nm may be selected as the third wavelength component, and a wavelength component of about 800 nm may be selected as the fourth wavelength component.

The peak analysis portion 310 has: a peak detection portion 370 for scanning the spectroscopic data retained in the spectroscopic data memory 302 and detecting the peak of the light emitted from the measurement region 102; and a peak characteristic quantity extracting portion 372 for extracting a characteristic quantity of the peak detected by the peak detection portion 370 based on the spectroscopic data. Specifically, the characteristic quantity of the peak is an emerging time point of the peak, wavelength, height of the peak which is intensity of a wavelength component at a top of the peak (hereinafter, referred to as the "peak intensity"), spectral line width, shift quantity and line shape.

The peak analysis portion 310 further has a knocking detection portion 373 for determining whether or not the knocking is generated based on a characteristic quantity of a peak emerging in a fifth wavelength component corresponding to light emitted from a subsidiary product generated by an influence of pressure wave when the knocking is generated, or light emitted from a component generating a temporal change in light emitted from a product due to a reaction, and in the case where the knocking is generated, outputting a signal for notifying that the knocking is generated. The fifth wavelength component is a wavelength component corresponding to the light emitted from OH* for example. When the pressure wave is generated by the knocking, OH* is generated in a region having a high temperature and high pressure due to an influence thereof, and the light emitted from OH* is sometimes detected in a region where the combustion reaction is not occurred. In such a case, there is a difference between an emerging time point of a peak in a wavelength component corresponding to light emitted from $C_2$*, CN* and/or CH* for example generated by the combustion reaction (hereinafter, referred to as the "sixth wavelength component") and an emerging time point of the peak in the wavelength component corresponding to the light emitted from OH*. By the influence of the pressure wave, the intensity of the light emitted from OH* is sometimes stepwise changed like waves over time. The knocking detection portion 373 determines whether or not the knocking is generated based on such a temporal change of the light generated when the knocking is generated.

The peak analysis portion 310 further has a statistical processing portion 374 for performing statistical processing for the characteristic quantities of the peaks extracted by the peak characteristic quantity extracting portion 372 and generating information on the characteristic of the light emitted from a measurement position (hereinafter referred to as the "measured light characteristic information") as a result thereof. Specifically, the measured light characteristic information is the characteristic quantities of the peaks, a ratio between the characteristic quantities of the peaks, an average value, a square mean value, a variance, time variability or the like thereof.

The peak analysis portion 310 further has: a calibration information memory 376 for retaining calibration information on a relationship between the characteristic of the light emitted from the reaction region and a state and a characteristic of the reaction region; and a characteristic quantity analysis portion 232 for analyzing and converting the measured light characteristic information into information on the characteristic of the object to be measured based on the calibration information, and storing the information in the analysis result memory 312 as a result of the analysis based on the peak. The characteristic of the object to be measured is for example mass, a flow rate, a concentration, pressure, a temperature, a plasma characteristic evaluation value or the like of the object to be measured or temporal variation thereof, thickness of a reaction zone, reaching speed of the reaction or the like. The calibration information is a function, a correlation curve, a table or the like showing a relationship between the characteristics of the light emitted from the plasma and the characteristic of the object to be measured.

[Flow of Entire Processing]

Figure 7:
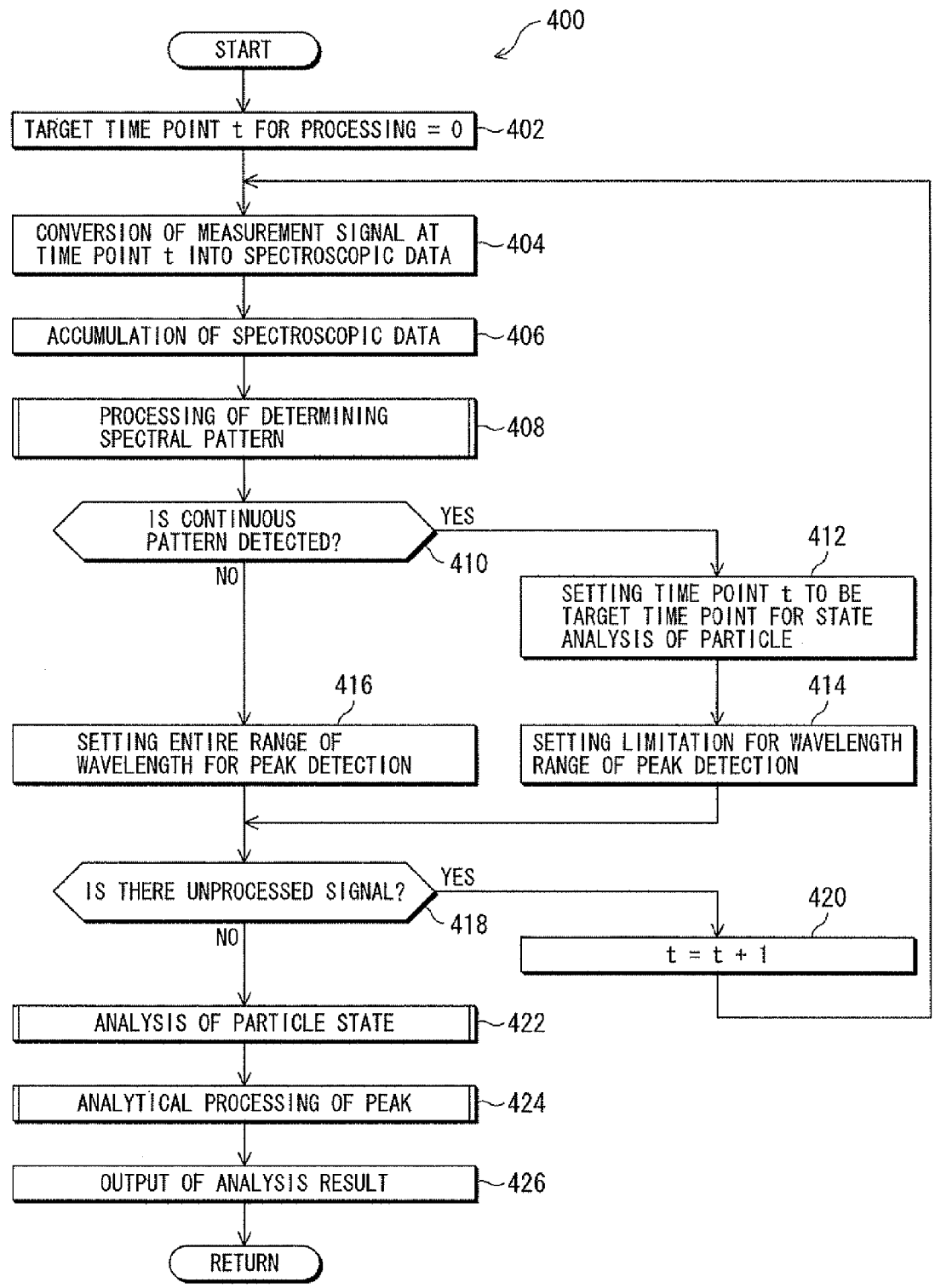
FIG. 7 A flowchart showing a control structure of entire processing of the reaction analysis apparatus in the measurement system.

FIG. 7 is a flowchart showing a control structure of the entire processing executed by the reaction analysis apparatus 114. With reference to FIG. 7, processing 400 is executed for the measurement signals 112A to 112N. When the processing 400 is started, a time point of an object to be processed is initialized to be zero in Step 402. In Step 404, the measurement signal at a time point t is amplified and digitalized so as to be converted into the spectroscopic data. In Step 406, the spectroscopic data converted in Step 404 is accumulated. In Step 408, processing of determining the spectral pattern is executed with using the spectroscopic data accumulated in Step 406. This processing will be described later with reference to FIG. 8.

In the following Step 410, it is determined whether or not the spectrum is determined to have the continuous spectral pattern in Step 408. If YES, the processing is moved to Step 412. Otherwise, the processing is moved to Step 416.

In Step 412, the time point t is set to be a target time point for a state analysis of the particle based on the continuous spectral pattern. In the following Step 414, in order to exclude the wavelength band under the influence of the blackbody radiation from the object to be processed in Step 418 described later, the first wavelength range is selected so as to limit a detection range of the peak, and then the processing is moved to Step 418. In the case where the processing is moved to Step 416, the second wavelength range is selected and the entire wavelength band is set to be the detection range of the peak in Step 416, and then the processing is moved to Step 418.

In Step 418, it is determined whether or not the measurement signal corresponding to a time point after the time point t is given. When the measurement signal is given, the processing is moved to Step 420, one is added to the time point t, and the processing is returned to Step 404. Otherwise, the processing is moved to Step 422.

In Step 422, the state of the particle emitting the blackbody radiation is analyzed with using the spectroscopic data. This processing will be described later with reference to FIG. 9. In Step 424, the peak is analyzed on the spectroscopic data. This processing will be described later with reference to FIG. 10. In Step 426, information obtained as a result of the processing in Steps 422 and 424 is outputted as an analysis result and this processing is completed.

[Spectral Pattern Analysis Processing]

Figure 8:
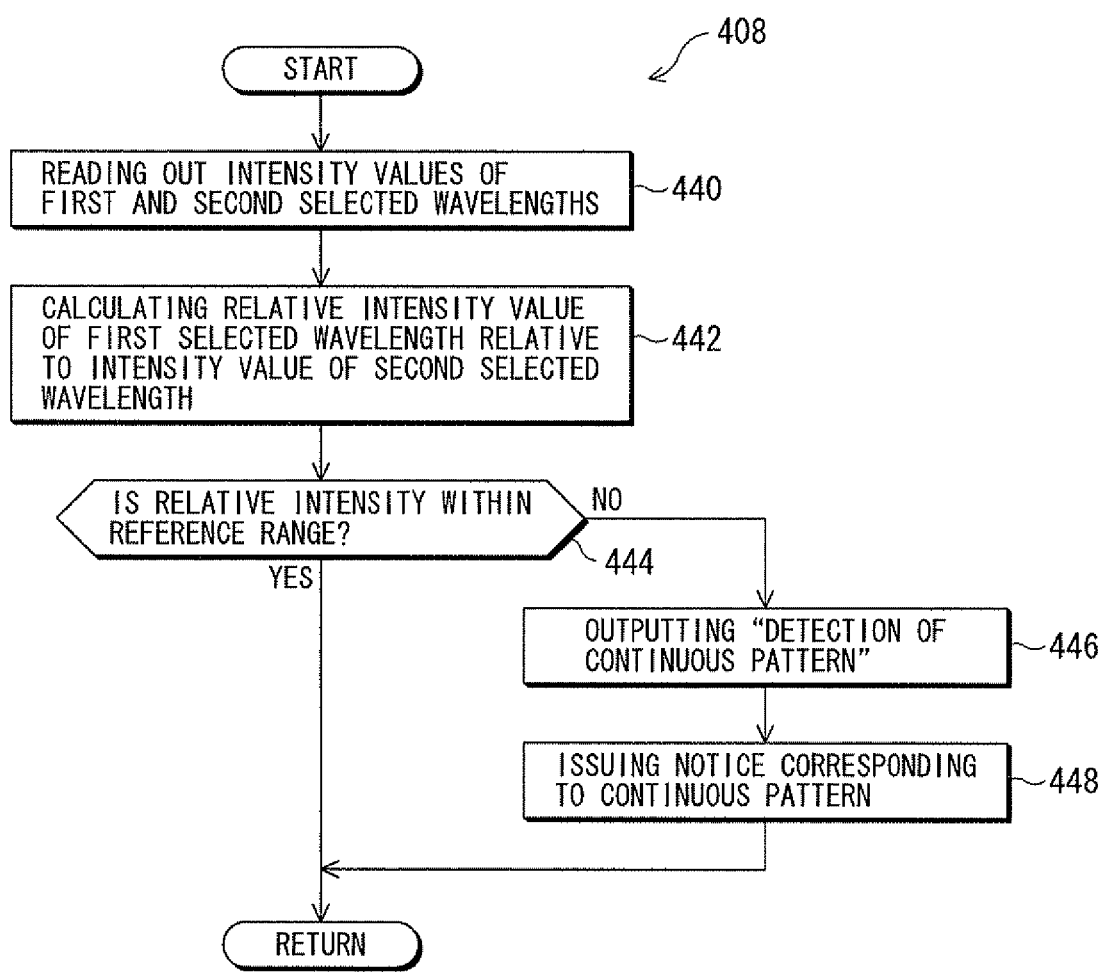
FIG. 8 A flowchart showing a control structure of spectral pattern determination processing in the measurement system.

FIG. 8 is a flowchart showing a control structure of the spectral pattern analysis processing executed in Step 408 mentioned above (refer to FIG. 7). With reference to FIG. 8, when processing 408 is started, intensity values of the first and second selected wavelengths are read out from the spectroscopic data accumulated in Step 406 (refer to FIG. 7) in Step 440. In Step 442, the first intensity value is divided by the second intensity value so as to calculate the relative intensity.

In Step 444, it is determined whether the relative intensity calculated in Step 442 is a value within a predetermined reference range or a value out of the reference range. When the relative intensity is the value within the reference range, the spectral pattern determination processing 408 is finished. When the relative intensity is the value out of the reference range, the processing is moved to Step 446. In Step 446, a value corresponding to the fact that the continuous spectral pattern is detected in the spectrum to be determined is outputted. In the following Step 448, notice corresponding to the continuous spectral pattern is issued and the spectral pattern determination processing 408 is finished.

[Particle State Analysis Processing]

Figure 9:
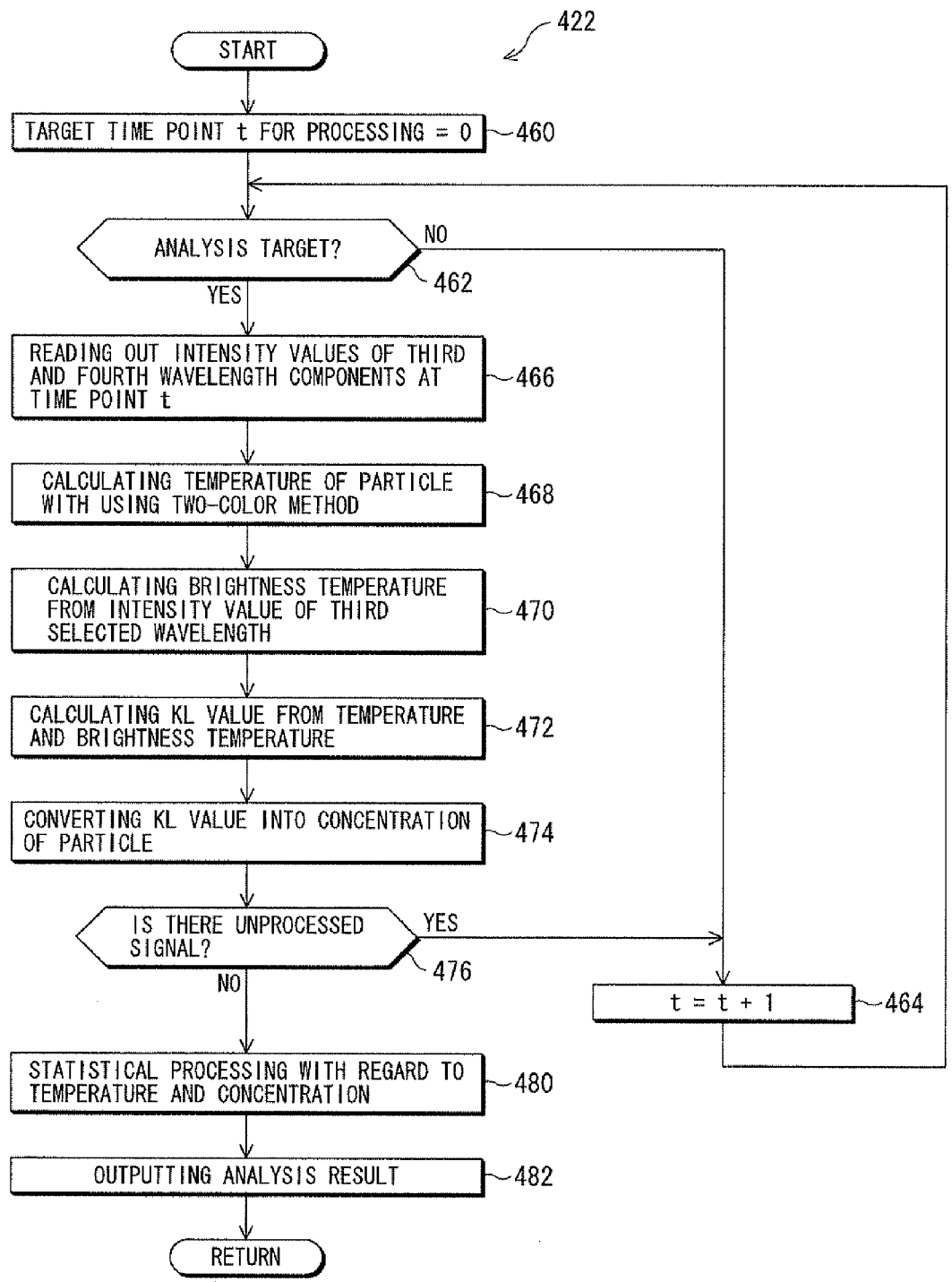
FIG. 9 A flowchart showing a control structure of a state analysis of a particle in the measurement system.

FIG. 9 is a flowchart showing a control structure of the particle state analysis processing executed in Step 422 mentioned above (refer to FIG. 7). With reference to FIG. 9, when processing 412 is started, the target time point t for the processing is initialized to be zero in Step 460. In Step 462, it is determined whether or not the time point t is set as the target time point for the analysis by Step 412 of the processing shown in FIG. 7. If YES, the processing is moved to Step 466. Otherwise, the processing is moved to Step 464, one is added to the time point t in Step 478, and the processing is returned to Step 462.

In Step 466, the intensity values of the third and fourth wavelength components at the time point t are read out from the spectroscopic data accumulated in Step 404 (refer to FIG. 7). In Step 468, a temperature of the particle emitting the light of the blackbody radiation is calculated from the intensity values of the third and fourth wavelength components read out in Step 466 with using a two-color method.

In Step 470, a brightness temperature corresponding to the third wavelength component is calculated from the temperature calculated in Step 468 and the intensity value of the third wavelength component based on Planck's radiation law. In the following Step 472, a so-called KL value, that is, the product of emissivity and thickness of a reaction field is calculated from the temperature calculated in Step 468 and the brightness temperature calculated in Step 470. In Step 474, the KL value calculated in Step 472 is converted into the concentration of the particle. In Step 476, it is determined whether or not the spectroscopic data at the time point after the time point t is accumulated. If YES, the processing is moved to Step 464. Otherwise, the processing is moved to Step 480.

In Step 480, the statistical processing in time direction is executed with regard to the temperature and the concentration of the particle calculated in a series of processing in Steps 460 to 476, and an average value, a standard deviation value, a temporal change value and the like of these values are determined. In Step 482, the temperature and the concentration of the particle calculated in a series of processing in Steps 460 to 476 and a statistical quantity thereof determined in Step 480 are outputted and stored as the analysis result, and the particle state analysis processing 422 is finished.

[Peak Analysis Processing]

Figure 10:
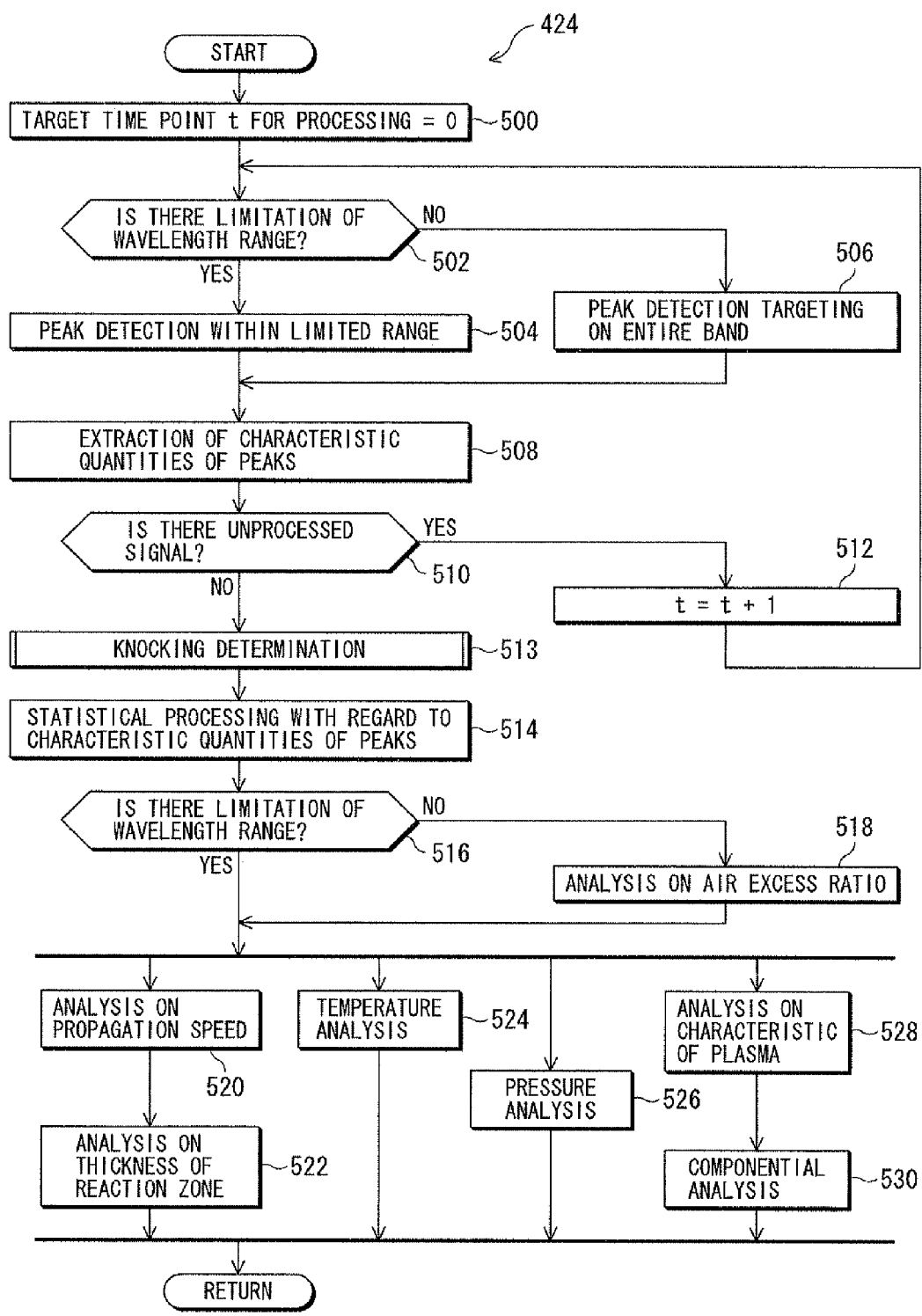
FIG. 10 A flowchart showing a control structure of peak analysis processing in the measurement system.

FIG. 10 is a flowchart showing a control structure of the peak analysis processing executed in Step 424 mentioned above (refer to FIG. 7). With reference to FIG. 10, when peak analysis processing 424 is started, the target time point t for the processing is initialized to be zero in Step 500. In Step 502, it is determined whether or not the wavelength range set in Step 414 or 416 (refer to FIG. 7 for both steps) with regard to the time point t is a limited range. If YES, the processing is moved to Step 504. Otherwise, the processing is moved to Step 506.

In Step 504, the spectroscopic data is scanned in the limited wavelength band, all the peaks in the above range are detected, and the processing is moved to Step 508. In Step 506, the spectroscopic data of the entire wavelength band is scanned, all the peaks in the above range are detected, and the processing is moved to Step 508.

In Step 508, based on the spectroscopic data, the emerging time point of the peak, the wavelength, the peak intensity, spectral line width, shift quantity and line shape with regard to the peaks detected in Step 504 or 506 are identified and stored as the characteristic quantities of the peaks.

In Step 510, in Step 474, the KL value calculated in Step 472 is converted into the concentration of the particle. In Step 476, it is determined whether or not the spectroscopic data at the time point after the time point t is accumulated. If YES, the processing is moved to Step 464, one is added to the target time point t for the processing, and the processing is returned to Step 502. Otherwise, the processing is moved to Step 513.

In Step 513, knocking determination processing for determining whether or not the knocking is generated based on the characteristic quantities of the peaks is executed. This processing will be described later with reference to FIG. 11. In the following Step 514, based on the characteristic quantities of the peaks identified by a series of processing in Steps 500 to 512, the statistical processing with regard to the characteristic quantities of the peaks is executed and the measured light characteristic information is generated. The generated measured light characteristic information is stored.

In Step 516, it is determined whether or not the wavelength range is limited as well as Step 502. If NO, the processing is moved to Step 518. By collating a ratio of the peak intensities among the measured light characteristic information and a statistical value thereof with a prepared calibration curve, the analysis on the air excess ratio is executed and a result thereof is outputted. At this time, the analysis result on the air excess ratio may be outputted after converting into information on a local equivalent ratio or a local air-fuel ratio.

When the processing in Step 516 or 518 is finished, analysis processing in Steps 520 and 522, Step 524, Step 526, Steps 528 and 530 and Step 532 are executed in parallel.

In Step 520, based on information on a prepared position of a starting point for the reaction in the reaction region and a start time point of the reaction, information on the measurement position and the emerging time point of the peak among the measured light characteristic information, propagation speed of the reaction in the reaction region and a statistical quantity thereof are analyzed and an analysis result thereof is outputted and stored.

In Step 522, the propagation speed analyzed in Step 520 is multiplied by width of the peak in time axis direction so as to calculate the thickness of the reaction zone. Further, based on the statistical quantity of the propagation speed and the statistical quantity of the peak width in time axis direction, a statistical quantity of the thickness of the reaction zone is analyzed. The thickness of the reaction zone and the statistical quantity thereof are outputted and stored as the analysis result.

In Step 524, with regard to the peaks corresponding to a plurality of wavelength components contained in the light emitted from a single radical or plasma, based on a peak intensity ratio of the peaks and statistical quantity thereof, a rotation temperature of the radical or the plasma is analyzed and the rotation temperature and a statistical quantity thereof are outputted and stored as an analysis result.

In Step 526, the spectral line width of the peaks is converted into pressure at the measurement position, and the pressure is analyzed based on the statistical quantity of the spectral line width. Results of the analysis on the pressure at the measurement position and the pressure based on the statistical quantity are outputted and stored as an analysis result.

In Step 528, a characteristic of the radical or the plasma at the measurement position is identified from the wavelength of the peak and the shift quantity, and mass, a flow rate and a numerical quantity of a radical or plasma having the characteristic identified from the peak intensity and the statistical quantity thereof and statistical quantities thereof are calculated. A characteristic evaluation value, the mass, the flow rate and the numerical quantity of the radical or the plasma and statistical quantities thereof are stored as an analysis result. In the following Step 530, based on the analysis result in Step 528, a componental analysis such as a molecular analysis and an elemental analysis is executed and a result thereof is outputted and stored as an analysis result.

[Knocking Determination Processing]

Figure 11:
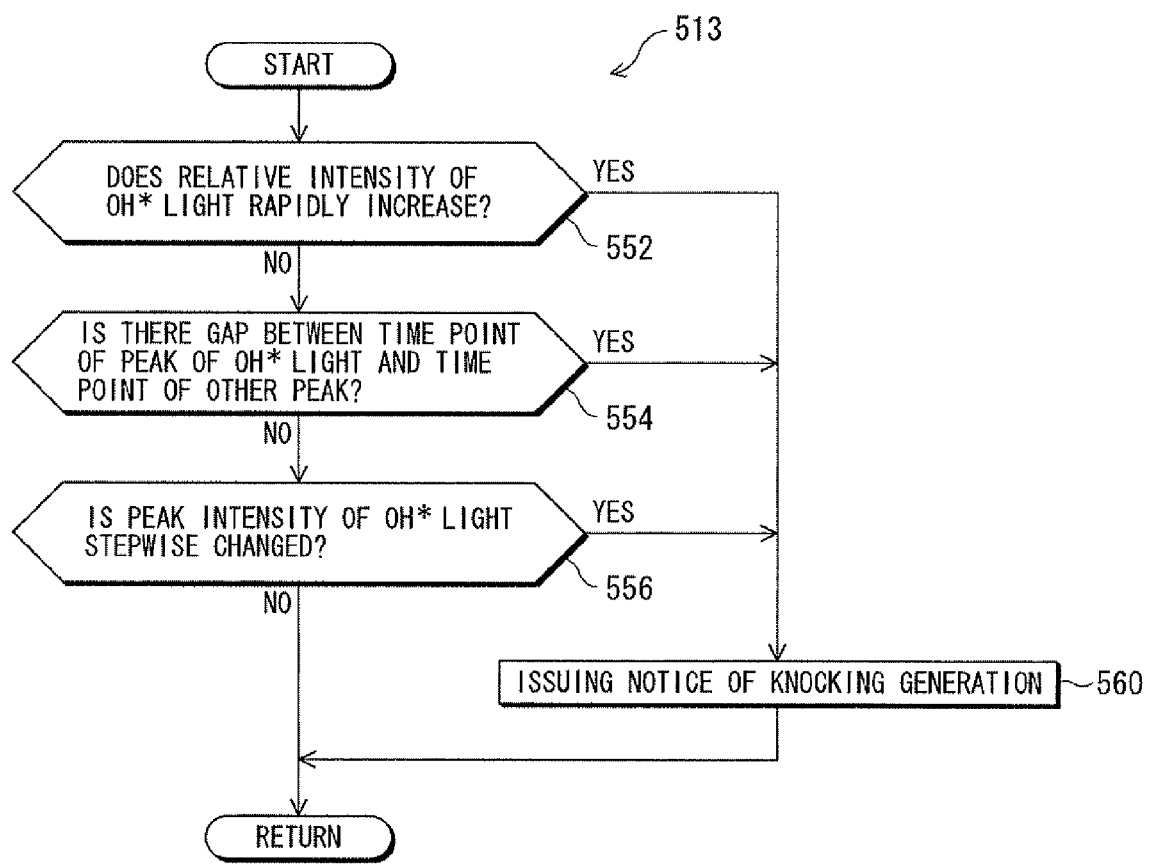
FIG. 11 A flowchart showing a control structure of knocking determination processing in the measurement system.

FIG. 11 is a flowchart showing a control structure of the knocking determination processing executed in Step 513 mentioned above (refer to FIG. 10). With reference to FIG. 11, when knocking determination processing 513 is started, it is determined whether or not intensity of the fifth wavelength component is rapidly increased in comparison to the sixth wavelength component in Step 552. Specifically, it is determined whether or not the peak emerges in the sixth wavelength component in a time range when the peak emerges in the fifth wavelength component. If NO, it is determined that the intensity of the fifth wavelength component is rapidly increased and thus the processing is moved to Step 560. If YES, it is determined that the intensity is not rapidly increased and thus the processing is moved to Step 554.

In Step 554, it is determined whether or not there is a gap between the emerging time point of the peak in the fifth wavelength component and the emerging time point of the peak in the sixth wavelength component. If YES, the processing is moved to Step 560. Otherwise, the processing is moved to Step 558.

In Step 558, it is determined whether or not the intensity of the fifth wavelength component is stepwise changed in the time range when the peak emerges in the fifth wavelength component. If YES, the processing is moved to Step 560. Otherwise, this processing is finished.

In Step 560, notice indicating that the knocking is generated is issued and this processing is finished.

[Action]

Hereinafter, an action of the measurement system according to the present embodiment will be exemplified. With reference to FIG. 2, the optical element 104 of the measurement system 100 is arranged so that the light from a desired measurement position is incident on the optical element 104, and the measurement is started in that state. With reference to FIG. 3, when the light emitted from the object points $O_1$, $O_2$, $O_3$, $O_4$, $O_5$ to $O_n$ in the reaction region is incident on the optical element 104, the light passes through the first region 140A of the first surface 140 of the optical element 104, goes through the medium between the first surface 140 and the second surface 142, and is reflected on the first region 142A of the second surface 142. The light reflected on the first region 142A of the second surface 142 is reflected on the second region 140B of the first surface 140, emitted through the second region 142B of the second surface 142) and respectively focused on the incident end surfaces of the optical fibers 108A to 108N via the stray light aperture 150. The focused light is incident on the fibers 108A to 108N respectively and emitted from the end surfaces on the side of the spectrometers 110A to 110N (refer to FIG. 2) via the optical fibers 108A to 108N.

With reference to FIG. 4, the light incident on the spectrometer 110A is converted into the parallel light by the collimator 170, reflected by the first mirror 172 and the second mirror 174, and then reaches to the spectroscopic element 176. Spectroscopy is performed on the light reaching to the spectroscopic element 176 so as to form the spectral light by the spectroscopic element 176 and reaches to the light detector 180 via the third mirror 178. The light detector 180 successively performs photoelectric conversion on the light reaching to the light receiving positions and outputs the measurement signal 112A showing a reaching position of the light at that time point and the intensity of the light at the position. The spectrometers 110A to 110N shown in FIG. 2 execute the same action as the above action and output the measurement signals 112A to 112N corresponding to the incident light respectively. The outputted measurement signals 112A to 112N are given to the reaction analysis apparatus 114.

When the reaction analysis apparatus 114 receives the measurement signals 112A to 112N, the reaction analysis apparatus 114 executes the following actions with regard to the measurement signals 112A to 112N.

With reference to FIG. 6, the measurement signal inputted to the reaction analysis apparatus 114 is given to the signal conversion portion 300. The signal conversion portion 300 responds to the fact that the measurement signal is given, successively amplifies and digitalizes the measurement signal so as to convert the signal into the spectroscopic data, and stores the spectroscopic data in the spectroscopic data memory 302.

When the spectroscopic data is stored in the spectroscopic data memory 302, the first intensity value obtaining portion 330 and the second intensity value obtaining portion 332 of the spectral pattern determination portion 304 successively read out and give the intensity values of the first and second selected wavelengths from the spectroscopic data to the relative intensity calculating portion 334. The relative intensity calculating portion 334 divides the given first intensity value by the second intensity value so as to calculate the relative intensity successively. The calculated relative intensity is successively given to the determination portion 338. The determination portion 338 compares the given relative intensity and the reference value retained in the reference value memory 336 and determines whether or not the relative intensity is within the predetermined reference range. When the relative intensity is not within the reference range, the determination portion 338 determines that the spectrum at the target time point which is determined is the continuous spectral pattern, and outputs the signal showing that the time point which is determined and the fact that the time point is the continuous spectral pattern to the output portion 316 and the processing selection portion 306. When receiving the input of this signal, the output portion 316 issues and outputs the notice of the soot generation, the notice of the fuel premixing failure, the generation of the luminous flame or the like as the analysis result 116.

The processing selection portion 306 selects the analysis processing for the spectroscopic data at the time point based on the signal from the determination portion 338. That is, for the time point determined to be the continuous spectral pattern, the analyses by both the continuous pattern analysis portion 308 and the peak analysis portion 310 are selected, and further the wavelength range of the peak to be analyzed by the peak analysis portion 310 is limited to the range which is not heavily influenced by the continuous spectral pattern. For other time points, the analysis only by the peak analysis portion 310 is selected, and further the entire wavelength range on the spectroscopic data is specified as the wavelength range of the peak to be analyzed by the peak analysis portion 310. The processing selection portion 306 generates and gives the instruction of the analysis performed by the continuous pattern analysis portion 308 and the peak analysis portion 310 based on this selection result to the continuous pattern analysis portion 308 and the peak analysis portion 310.

When the instruction from the processing selection portion 306 is given to the continuous pattern analysis portion 308, the data reading portion 350 reads out the intensity of the third wavelength component and the intensity of the fourth wavelength component at the time point when the processing by the continuous pattern analysis portion 308 is selected from the spectroscopic data memory 302 while following the instruction, and successively gives the intensities to the temperature calculating portion 352 and the concentration calculating portion 354. The temperature calculating portion 352 calculates the temperature of the particle emitting the light of the blackbody radiation from the intensity values of the third and fourth wavelength components with using the two-color method. The temperature calculating portion 352 stores the value of the calculated temperature in the analysis result memory 312 and further gives this value to the concentration calculating portion 354. The statistical processing with regard to the temperature is executed in time direction and the result thereof is stored in the analysis result memory 312. The concentration calculating portion 354 calculates the brightness temperature corresponding to the third wavelength component from the intensity value of the third wavelength component. The KL value is calculated from the brightness temperature and the temperature given from the temperature calculating portion 352. Further, the KL value is converted into the concentration of the particle. The concentration calculating portion 354 stores the calculated concentration value of the particle in the analysis result memory 312. The concentration calculating portion 354 performs the statistical processing with regard to the concentration in time direction, and stores the result thereof in the analysis result memory 312.

When the instruction from the processing selection portion 306 is given to the peak analysis portion 310, the peak detection portion 370 scans the spectroscopic data stored in the spectroscopic data memory 302 in wavelength direction and time direction, and determines whether or not there is the peak at each time point. However, for the time point when the wavelength range to be processed is limited by the instruction from the processing selection portion 306, the scanning is only executed within the limited wavelength range. The peak detection portion 370 adds the result of this determination to the spectroscopic data and gives the result to the peak characteristic quantity extracting portion 372.

When the spectroscopic data with the detection result of the peak is given from the peak detection portion 370, the peak characteristic quantity extracting portion 372 identifies the emerging time point, the wavelength and the peak intensity of the detected peaks based on this data. The peak characteristic quantity extracting portion 372 further scans the data around the top of the peak and identifies the spectral line width of the peak, the shift quantity and the line shape for each peak. The identified information is given to the knocking detection portion 373 and the statistical processing portion 374 as the characteristic quantity of each peak.

The knocking detection portion 373 pays attention to the fifth wavelength component among the given characteristic quantities of the peaks, and determines whether or not the knocking is generated as below. That is, in the case where the peak does not emerge in the sixth wavelength component in the time range when the peak emerges in the fifth wavelength component, or in the case where the peak emerges in the sixth wavelength component in the time range but there is a gap in terms of the emerging time point of the peak, or in the case where the intensity of the fifth wavelength component is stepwise changed in the time range, it is determined that the knocking is generated. In the case where it is determined that the knocking is generated, the knocking detection portion 373 outputs the signal showing the generation of the knocking to the output portion 316. When receiving the input of this signal, the output portion 316 issues and outputs the notice of the generation of the knocking as the analysis result 116.

The statistical processing portion 374 calculates the ratio between the characteristic quantities of the peaks and the like from the characteristic quantities of the peaks. The statistical processing portion 374 further performs the statistical processing for the characteristic quantities and the ratio thereof, and calculates the average value, the square mean value, the variance and the time variability thereof. The statistical processing portion 374 gives the characteristic quantities of the peaks, the ratio of the characteristic quantities and the result of the statistical processing for the characteristic quantities and the ratio, to the characteristic quantity analysis portion 378 as the measured light characteristic information.

The characteristic quantity analysis portion 378 responds to the fact that the measured light characteristic information is given from the statistical processing portion 374, executes the following analysis based on the calibration information retained in the calibration information memory 376 and converts this information into the measured object information. However, the analysis processing performed with using the characteristic quantity of the peak possibly emerging out of the target range for the peak detection is not executed.

That is, the characteristic quantity analysis portion 378 collates the ratio of the peak intensity among the measured light characteristic information and the statistical value thereof with configuration information, thereby executes the analysis on the air excess ratio and stores the result thereof in the analysis result memory 312. At this time, the analysis result on the air excess ratio may be stored in the analysis result memory 312 after converting into the information on the local equivalent ratio or the local air-fuel ratio. However, in the case where the reaction in the reaction region is the combustion of the hydrocarbon fuel as shown in FIG. 1, the wavelength component of the light emitted from $C_2^*$ and the wavelength component of the luminous flame are overlapped with each other. Therefore, when the luminous flame is generated, it is difficult to obtain the information on the peak corresponding to the light emitted from $C_2^*$. That is, the characteristic quantity analysis portion 378 does not execute the analysis on the air excess ratio at the time point when the luminous flame is generated.

The characteristic quantity analysis portion 378 executes the analysis on the propagation speed of the reaction in the reaction region and the statistical quantity thereof based on the position of the starting point for the reaction in the reaction region and the start time point of the reaction, the measurement position and the emerging time point of the peak, and stores the analysis result thereof in the analysis result memory 312.

The characteristic quantity analysis portion 378 multiplies the propagation speed by the width of the peak in time axis direction so as to calculate the thickness of the reaction zone. Further, based on the statistical quantity of the propagation speed and the statistical quantity of the peak width in time axis direction, the analysis on the statistical quantity of the thickness of the reaction zone is executed. The thickness of the reaction zone and the statistical quantity thereof are stored in the analysis result memory 312.

With regard to the peaks corresponding to a plurality of the wavelength components contained in the light emitted from the single radical or the plasma, the characteristic quantity analysis portion 378 executes the analysis on the rotation temperature of the radical or the plasma based on the peak intensity ratio of the peaks and the statistical quantity thereof, and stores the temperature and the statistical quantity thereof in the analysis result memory 312.

The characteristic quantity analysis portion 378 converts the spectral line width of each peak into the pressure at the measurement position, executes the analysis on the pressure based on the statistical quantity of the spectral line width, and stores the results of the analysis on the pressure based on the pressure at the measurement position and the statistical quantity in the analysis result memory 312.

The characteristic quantity analysis portion 378 identifies the characteristic of the radical or the plasma at the measurement position from the wavelength of the peak and the shift quantity, calculates the mass, the flow rate and the numerical quantity of the radical or the plasma having the characteristic identified from the peak intensity and the statistical quantity thereof and statistical quantities thereof, and stores the characteristic evaluation value, the mass, the flow rate and the numerical quantity of the radical or the plasma and statistical quantities thereof in the analysis result memory 312 as the analysis result. Further, based on this analysis result, the componential analysis such as the molecular analysis and the elemental analysis is executed and the result thereof is stored in the analysis result memory 312.

The characteristic quantity analysis portion 378 executes processing of checking whether or not there is reaction abnormality, such as the knocking, at the measurement position. A detection result thereof is stored in the analysis result memory 312.

The analysis results by the continuous pattern analysis portion 308 and the peak analysis portion 310 are stored in the analysis result memory 312. When the user interface 314 receives the operation of requiring an output of desired measured object information by the user, the user interface 314 gives the instruction corresponding to this operation to the output portion 316. The output portion 314 reads out the information corresponding to the requirement of the user from the analysis result memory 312 while following the given instruction, and outputs the information as the analysis result 116.

As mentioned above, in the measurement system 100 according to the present embodiment, the optical element 104 focuses the light emitted from the measurement region 102. In this optical element 104, since the surfaces related to focusing are only the reflecting surface, the chromatic aberration is not generated. Therefore, it is possible to perform spectrometry with high spatial resolution, detection of the generation of the luminous flame, the soot and the like, detection of the knocking and various analyses on the reaction region. In the present embodiment, the time-series signal is generated as the measurement signal and the signal processing is executed in time series with using the time-series signal. Therefore, it is possible to obtain information on a time-series change of the reaction in the measurement region 102.

In the present embodiment, based on the relative intensity of the first wavelength component relative to the intensity of the second wavelength component obtained at the same time point by the spectrometry, it is determined that the light of the continuous spectral pattern is generated. The generation of the soot or the luminous flame, the fuel premixing failure or the like is detected with the determination result. Therefore, it is possible to detect the generation of the soot or the luminous flame, the fuel premixing failure or the like without being influenced by deterioration in performance of the optical element receiving the light due to adhesion of the soot or the like.

In the present embodiment, since an analysis method of the result of spectrometry is selected based on the above determination result, it is possible to avoid executing wasted processing and perform effective analysis processing in accordance with the light emitted at the measurement position. Further, by effectively utilizing the result of spectrometry without waste, it is possible to obtain more information from the measurement result.

In the present embodiment, the generation of the knocking is detected based on a relative relationship between the light emitted from OH* by the influence of the pressure wave accompanying the knocking and the light emitted from other radicals generated by the reaction and the temporal change of the light emitted from OH*. Therefore, in comparison to detection of the knocking from the pressure, the vibration or the like, it is possible to more directly detect the knocking, and reproducibility of the detection of the generation of the knocking is improved. It is also possible to detect the generation of the knocking without being influenced by the deterioration in the performance of the optical element receiving the light due to the adhesion of the soot or the like.

Modified Example 1

In the above embodiment, the optical element 104 is an optical system for focusing the light by reflection. However, an optical system, such as a convex lens, may be used instead of this optical element 104. Although, in this case, aberration due to the wavelength of the light is desirably reduced by various methods.

In the above embodiment, the end surfaces of the optical fibers 108A to 108N on the side of the optical element 104 are two-dimensionally arranged on the image formation surface of the optical element 104. However, the present invention is not limited to such an embodiment. The incident end surfaces of the optical fibers 108A to 108N may be three-dimensionally arranged. By this, it is possible to three-dimensionally measure and analyze the light emitted from the reaction region.

In the above embodiment, the spectrometers 112A to 112N perform spectrometry on the incident light and convert and output the spectral light obtained as a result into the electric signal by the light detector 180. However, the present invention is not limited to such an embodiment. When the reaction performed at the measurement position in the reaction region is already known, or when an objective of the measurement is to obtain information only on the reaction of an object having a predetermined plasma characteristic, the spectrometer may extract only a specific wavelength component among the light emitted from the reaction region and convert the wavelength component into the electric signal.

For example, the light detector 180 may be arranged at a position where only the specific wavelength component among the spectral light after spectroscopy passes through. When there are pluralities of desired wavelength components, a plurality of light detectors may be arranged at positions corresponding to the desired wavelength component respectively.

Figure 12:
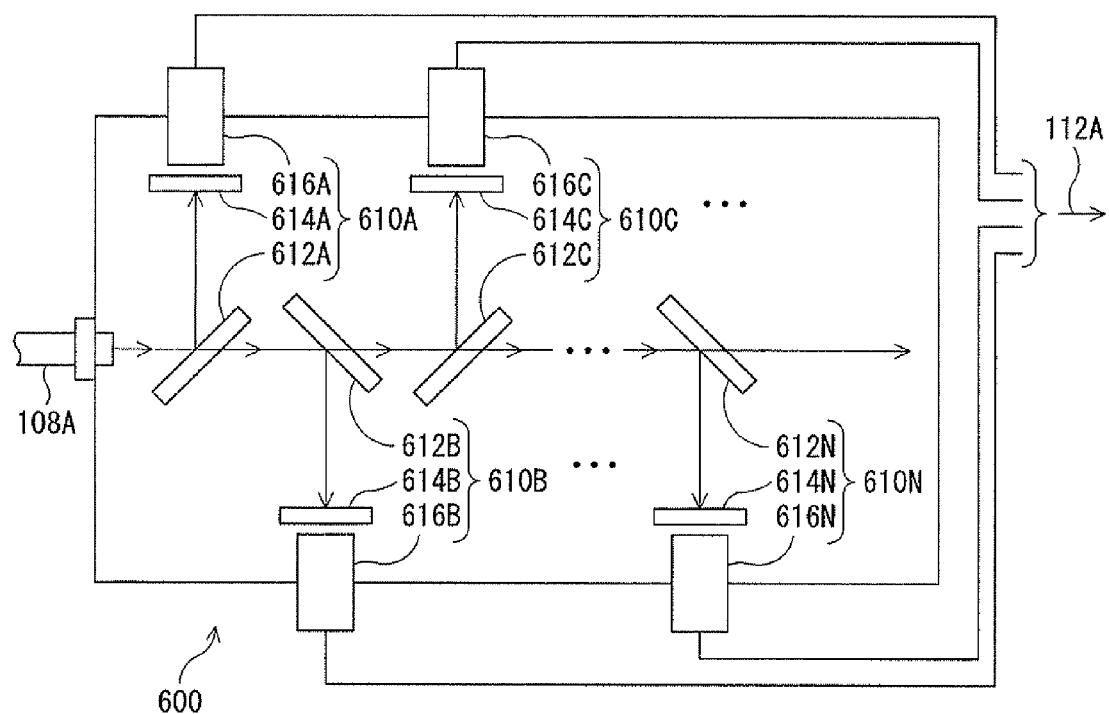
FIG. 12 A side view showing a configuration of the spectrometer of extracting only a specific wavelength component in the measurement system.

For example, only the specific wavelength component may be extracted by an optical element having a selective characteristic of permeability, reflection or absorption relative to the wavelength of the light or a combination of optical systems consisting of the above optical elements. FIG. 12 shows one example of a spectrometer of a configuration having such a function. With reference to FIG. 12, a spectrometer 600 is connected to the optical fiber 108A. This spectrometer 600 has a plurality of spectrometric units 610A, 610B, 610C to 610N for measuring intensity of light of wavelength which is preliminarily selected in accordance with the object to be measured (hereinafter, simply referred to as the "selected wavelength"). For example, when the reaction in the reaction region is the combustion reaction of mixture of the hydrocarbon fuel and the air, the wavelength of the light generated from OH*, the light generated from CH*, the light generated from CN*, the light generated from $C_2$* and the like, and two wavelength used for calculating the temperature and the concentration of the soot are respectively selected for the selected wavelength. It should be noted that in the case where this spectrometer 600 is applied, wavelength other than the selected wavelength is selected for wavelength of a laser flux.

The spectrometry unit 610A has: a dichroic mirror 612A arranged on the optical axis of the light emitted from the optical fiber 108A so as to make a predetermined angle relative to this optical axis, having a reflection characteristic relative to an optic component in a predetermined band including the selected wavelength of the spectrometry unit 610A and a permeability characteristic relative to an optic component in other wavelength band including the wavelength of the laser flux and the selected wavelength by other than the spectrometry unit 610A; a filter 614A arranged on an optical axis of the light reflected by the dichroic mirror 612A, having the permeability characteristic relative to an optic component of the selected wavelength of the spectrometry unit 610A; and a light detector 616A arranged on the opposite side of the filter 614A on the optical axis of the light reflected by the dichroic mirror 612A with respect to the dichroic mirror 612A.

Configurations of the spectrometry units 610B, 610C to 610N are the same as the configuration of the spectrometry unit 610A. However, wavelength characteristics of the dichroic mirror and the filter thereof are selected in accordance with the selected wavelength thereof.

This spectrometer 600 is operated as below. That is, when the light is incident from the optical fiber 108A, spectrometry is performed on the light by the dichroic mirrors 612A, 612B, 612C to 612N. Components in the wavelength band in the vicinity of the selected wavelength among the optic components after spectrometry pass through the filters 614A, 614B, 614C to 614N and reach the light detectors 616A, 616B, 616C to 616N respectively. The light detectors 616A, 616B, 616C to 616N respectively and sequentially convert and output the reaching optic components into the measurement signal 112A.

When the signal processing device 114 executes the determination and the analysis based on the measurement signal 112A outputted as above, there is no need for executing the detection of the peak and other processing with regard to the wavelength band other than the vicinity of the selected wavelength. Since an information quantity to be processed is reduced, the signal processing becomes more efficient so as to perform high-speed processing.

It should be noted that when there is no need for the analysis result based on the spectral line width, the shift quantity and the line shape in wavelength direction as the measured object information, the output signal of the light detectors 616A, 616B, 616C to 616N does not always contain the information on the light receiving position. In such a case, a photoelectron multiplier tube or the like may be applied as the light detectors 616A, 616B, 616C to 616N. Since the photoelectron multiplier tube has higher time responsiveness than an image sensor such as the CCD, it is possible to perform the measurement with high time resolution.

In such a spectrometer 600, the output signal of the light detectors 616A, 616B, 616C to 616N may be separately amplified and the amplified signal may be outputted as the measurement signal 112A. However, in such a case, there is a need for setting the reference value stored in the reference value memory 336 shown in FIG. 6 to be a value in accordance with an amplification factor of the signal.

In the above embodiment, the temperature and concentration analysis processing based on the continuous spectral pattern, and the analysis processing based on the peak are executed at a stage after the entire spectroscopic data is stored in the spectroscopic data memory 302 shown in FIG. 6. However, with regard to processing which does not require the statistical processing in time direction among the above analysis processing, at every time when the spectroscopic data corresponding to a time point is generated, the analysis based on the spectroscopic data at the time point may be executed. Further, the above analysis processing may be executed in real time. Furthermore, an analysis result obtained by such real-time processing may be outputted in real time.

In the above embodiment, the processing for the continuous spectral pattern due to the luminous flame in the combustion reaction is mainly described. However, in the present invention, it is possible to determine the continuous spectral pattern in other various reactions and select the analysis processing based on the determination. For example, in a reaction of radiating laser beam or the like to the reaction region and making a substance or the like in the region to be plasma, the light having the continuous spectral pattern is sometimes generated particularly in a short wavelength band at the very initial stage of the reaction. In such a case, when the first wavelength component, the second wavelength component and the reference value for determination are properly selected, it is possible to properly detect the initial stage of the reaction. With regard to the initial stage detected in such a way, the peak analysis processing may be omitted.

In the above embodiment, with reference to FIG. 6, the output portion 316 converts and outputs the result of the determination by the spectral pattern determination portion 304 and the result of the determination of the knocking by the peak analysis portion 310 into the information on the state of the measurement region 102, and reads out and outputs the measured object information retained in the analysis result memory 312. However, the signal processing portion 114 may further integrate the information to be outputted by the output portion 316 so as to generate and output new information. For example, when the reaction region is an region where the reaction is repeatedly generated in a fixed cycle such as a combustion chamber of an engine for an automobile, the analysis results may be integrated based on the information stored in the memory 312 for the measured object information so as to generate and output information on a relationship between the analysis result and the cycle of the reaction. Specifically, when information on a cycle change of the analysis result or the like is generated and outputted, it is possible to provide more understandable information on the reaction region. The information on the relationship between the analysis results is generated and outputted by comparing the analysis results to each other or analyzing relativity.

The disclosed embodiment is only an example and the present invention is not limited to the above embodiment. A scope of the present invention is shown in claims in consideration to detailed description of the invention, and includes equivalent meanings to wordings therein and all variations within the scope.

Modified Example 2

Time Division Function of Measurement Result
(Correspondence to Repeated Measurement, Multi-Point Measurement Unification and the Like)

Figure 13:
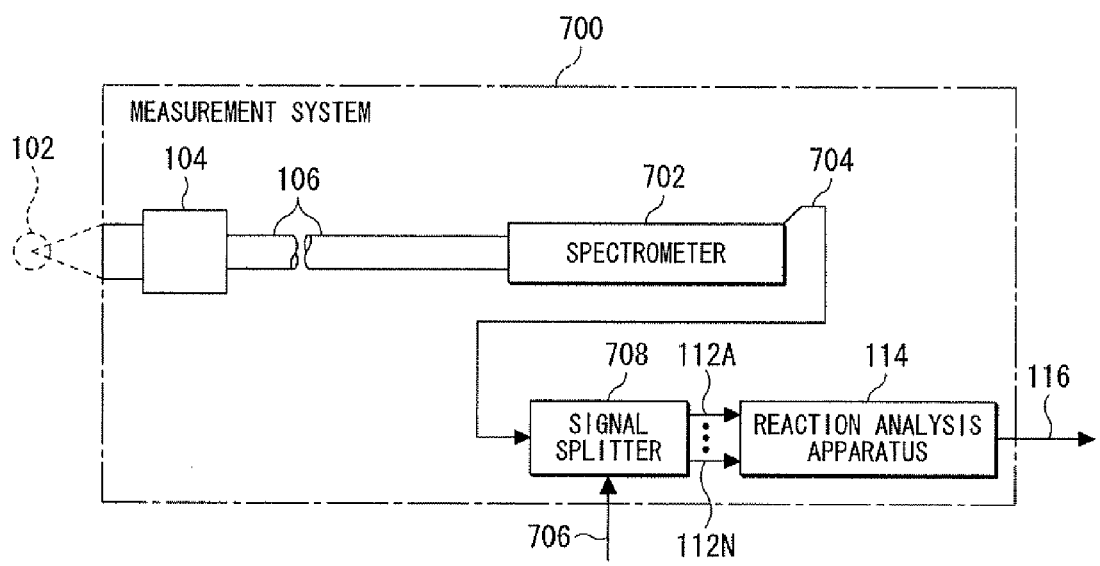
FIG. 13 A block view showing an entire configuration in a modified example 2 of the measurement system according to the present invention.

FIG. 13 shows a schematic configuration of the measurement system according to the present embodiment.

This system is provided with the optical element 104, the optical fiber cable 106 and the reaction analysis apparatus 114 as well as FIG. 1, and a spectrometer 702 directly connected to the optical fiber cable 106 and a signal splitter 708 connected to the spectrometer 702 and the reaction analysis apparatus 114.

Figure 14:
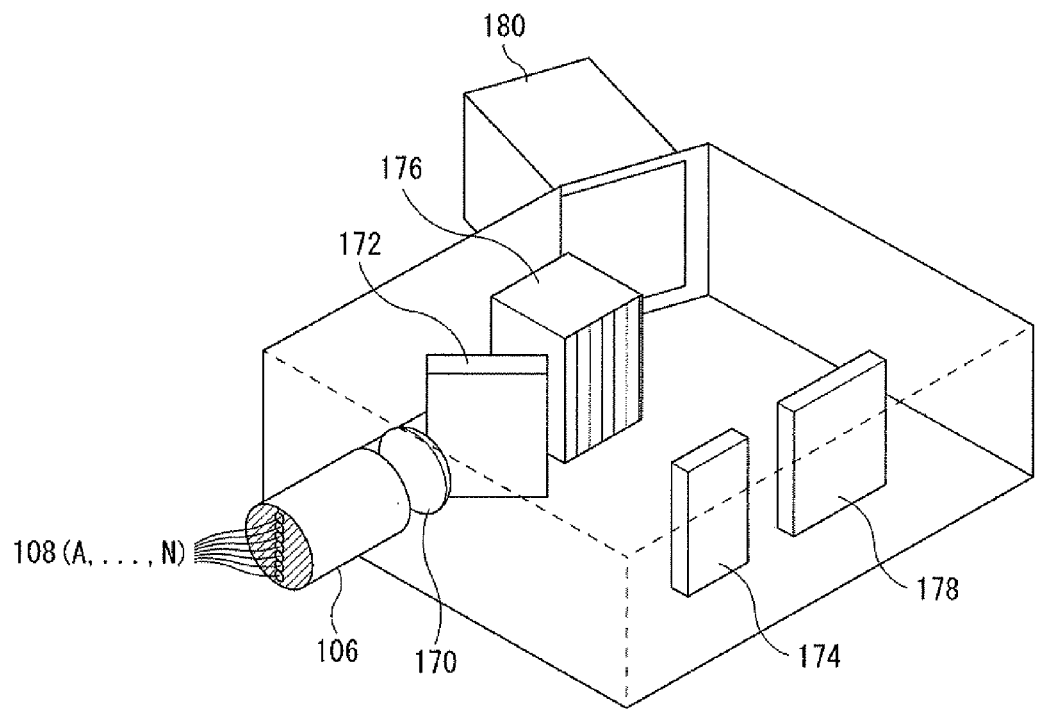
FIG. 14 A partial transparent perspective view showing a configuration of the spectrometer in the modified example 2 of the measurement system according to the present invention.

FIG. 14 shows an internal configuration of the spectrometer 702.

The spectrometer 702 has the same configuration as the spectrometer 110A shown in FIG. 4. However, the optical fiber cable 106 is directly connected to the spectrometer 702 instead of the optical fiber 108A to be connected to the spectrometer 110A. The optical fibers 108A to N are bundled in a row in the optical fiber cable 106. The optical fibers 108A to N are connected to the spectrometer 702 so as to be aligned in a row in parallel to the extending direction of slits of this optical grating 176. Thereby, with regard to the light incident from any of the optical fibers 108A to N on the spectrometer 702, the same wavelength component reaches to the same position of the light detector 180. Therefore, a signal 704 outputted from the spectrometer 702 is an overlapped spectroscopic result of the light from a plurality of the object points (O1 to On in FIG. 3) in the reaction region 102.

The signal splitter 706 shown in FIG. 13 generates the signals 112A to 112N corresponding to the object points O1 to On by dividing the signal 704 in time direction based on a predetermined external signal 706 and periodicity of the signal 704 from the spectrometer 702. It should be noted that the external signal here is, for example, a signal showing the number, the order or the like of the bundled optical fibers in the optical fiber cable 106.

Figure 15:
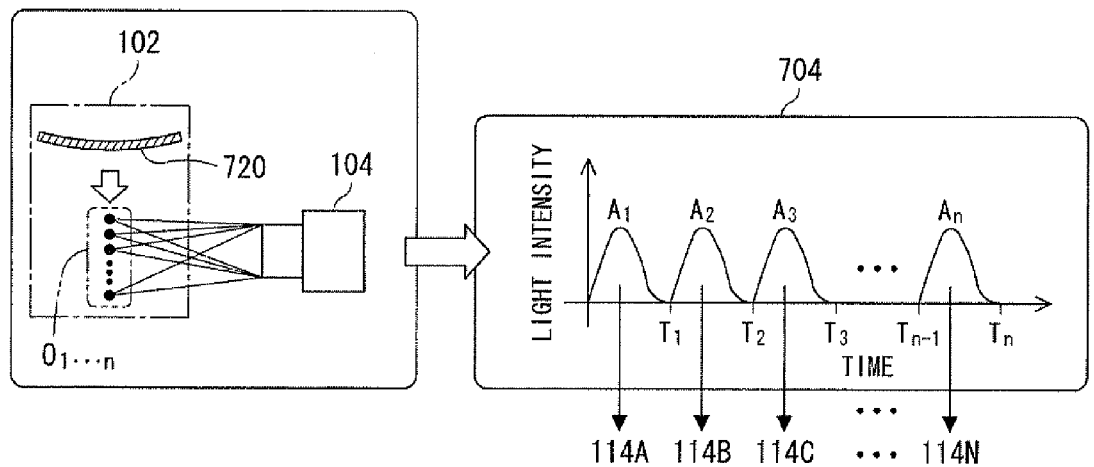
FIG. 15 A schematic view showing an outline of an action of the spectrometer in the modified example 2 of the measurement system according to the present invention.

FIG. 15 schematically shows a concept of generation of the signals 112A to 112N by the signal division in time direction. With reference to FIG. 15, a belt shape reaction region (hereinafter, referred to as the "reaction zone") 720 is moved so as to successively cross over the object points O1 to On. Intensity 722 of light introduced to the optical fibers 108A to N corresponding to the object points which are crossed over is enhanced at time points when the reaction zone 720 crosses over the object points O1 to On respectively. Therefore, there is a time difference between the light introduced from the optical fibers A to N to the spectrometer 702. The measurement result 704 by the spectrometer is an overlapped result thereof which is a signal of repeating an extremely large period (A1 to An) and an extremely small period (T1 to Tn) the same number of times as the number of the optical fibers. The signal splitter 708 divides the signal 704 in time direction at timing when the intensity of the signal 704 is extremely small (T1 to Tn). Based on the external signal 706, the divided signals are outputted as the signals 114A to N corresponding to the optical fibers 108A to N.

Figure 16:
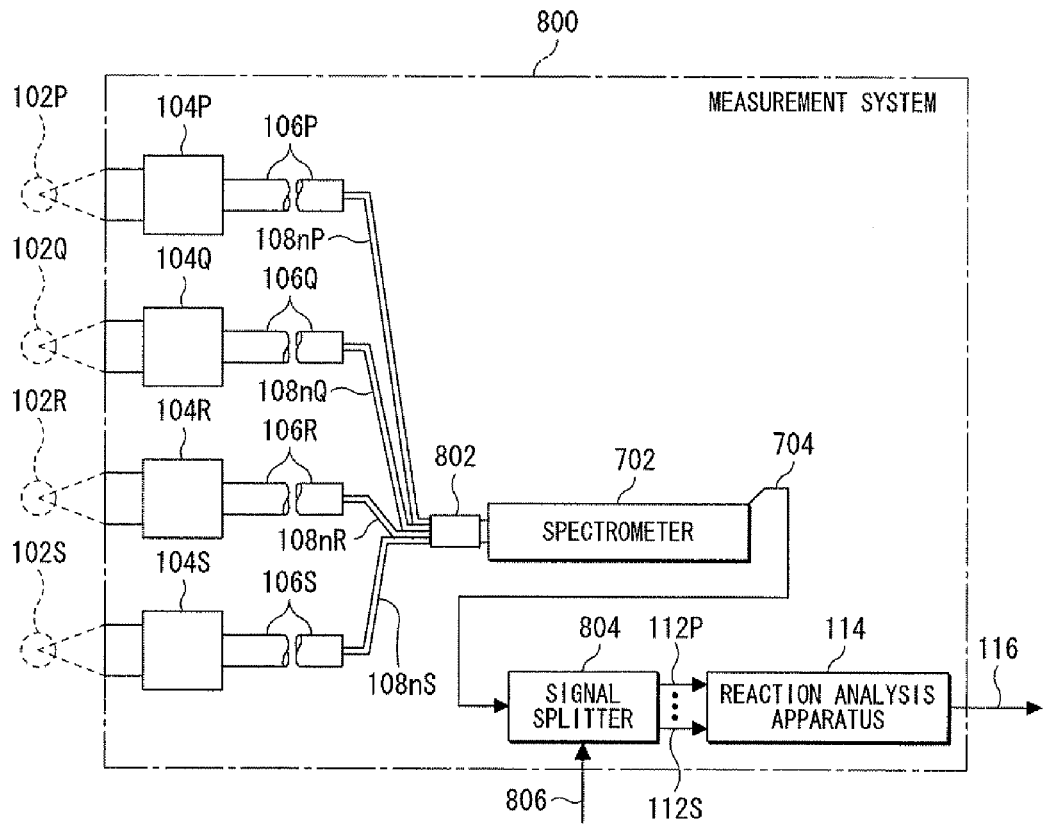
FIG. 16 A block diagram showing an entire configuration in the modified example 2 of the measurement system according to the present invention.

FIG. 16 shows a schematic configuration of a measurement system 800 according to a modified example of the present embodiment.

This measurement system 800 has: four optical elements 104P to S; and optical fiber cables 106P to S respectively connected to the optical elements. Predetermined optical fibers among the optical fibers bundled in the optical fiber cables 106P to S (optical fibers 108nP to 108nS) are bundled by a optical fiber bundle 802. The optical fiber bundle 802 is connected to the spectrometer 702 which is the same as in FIG. 13. The spectrometer 702 is connected to the reaction analysis apparatus 114 via a signal splitter 804.

An external signal 806 inputted to the signal splitter 804 is a signal showing the number, the order or the like of the optical element, for example. Alternatively, in the case of measurement of a multi-cylinder engine below, information on a crank angle may be the external signal 806. Hereinafter, an action example of performing a reaction analysis on cylinders targeting a four-cylinder engine with using this measurement system 800 will be shown.

In this action example, the optical elements 104P to S are installed in the cylinders of the engine. In this case, the signal splitter 804 receives a signal of the crank angle as the external signal 806. In the four-cylinder engine, ignition is performed in any one of the cylinders as the crank is rotated around 180 degrees. Combustion initiated by the ignition is finished within a period from an ignition time point to an end of 180 degrees rotation of the crank. The combustion is performed once in each of the cylinders as the crank is rotated around 720 degrees. The order of the cylinders where the ignition is performed is preliminarily fixed. Therefore, the cylinder where the combustion is performed is one of the four cylinders.

The light emitted from the optical elements 104P to S is superimposed and spectroscopy is performed on the light by the spectrometer 702. The signal 704 includes the result of spectrometry of the light generated by the combustion for the four cylinders. However, since the cylinder where the combustion is performed is one of the four cylinders as mentioned above, the signal is not overlapped. Assuming that the crank angle when the ignition is performed in one of the four cylinders is zero, the signal splitter 804 divides the signal into a section of the crank angle from 0 to 180 degrees, a section from 180 to 360 degrees, a section from 360 to 540 degrees and a section from 540 to 720 degrees. Numbers of the cylinders where the combustion is performed in the section are given to the divided signals so as to generate signals 112P to S. These signals 112P to S are given to the reaction analysis apparatus 114. As a result, the reaction analysis apparatus 114 performs the reaction analysis for each of the cylinders.

As mentioned above, the measurement system 800 realizes spectrometry and the reaction analysis for the cylinders of the multi-cylinder engine with one spectrometer. This contributes to downsizing of the measurement system and cost reduction. Since the number of spectrometer susceptible to the vibration in general and the number of constituent parts thereof are reduced, it is possible to decrease variation in a result due to an individual difference of the spectrometer or the like. With this measurement system 800, it is possible to collectively measure and analyze various information on the combustion reaction of the cylinders. By comparing the results of the reaction analysis on the cylinders, it is possible to obtain information on the variation and a change between the cylinders.

It should be noted that the spectrometer 600 shown in FIG. 12 (of a basic application) may be used instead of the spectrometer 700. In this case, there is no need for arranging the optical fibers in a row.

It should be noted that the signal splitter 708 may be built in the reaction analysis apparatus. For example, when reading out the data from the spectroscopic data memory 302 shown in FIG. 6, the signal splitter 708 may perform time division for the signal.

Modified Example 3

Exceptional Processing Function in Case of Performing LIBS, SIBS or the Like

Figure 17:
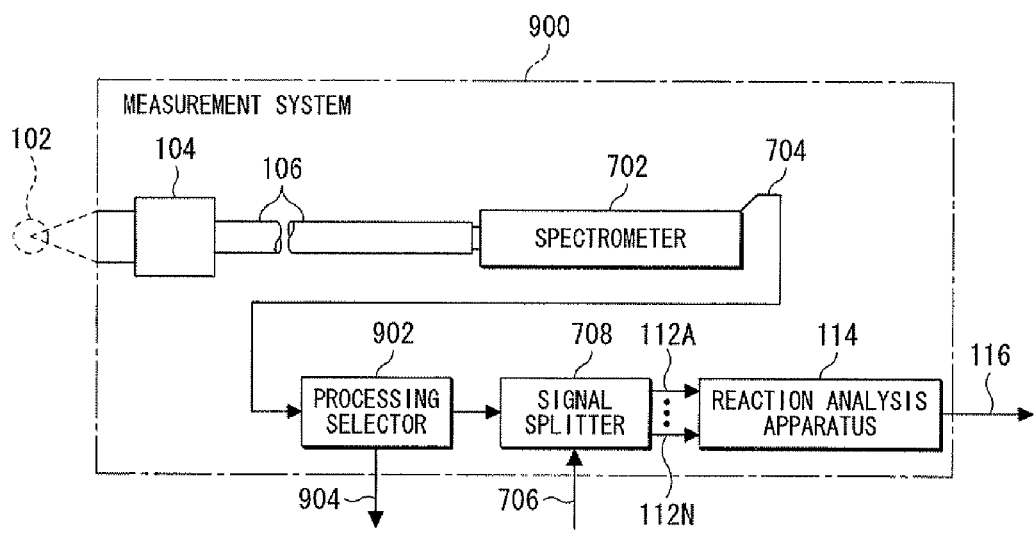
FIG. 17 A block diagram showing an entire configuration in a modified example 3 of the measurement system according to the present invention.

FIG. 17 shows a schematic configuration of a measurement system 900 in this embodiment.

In this measurement system 900, both the reaction such as the combustion, and plasma induction (breakdown) by laser are performed in the reaction region 102. In this measurement system 900, a processing selector 902 for selecting an output direction of the received signal in accordance with emission intensity of a specific wavelength component shown by the signal 704 is arranged on a signal path between the spectrometer 702 and the signal splitter 708 of the spectrometer 700 shown in FIG. 13.

The processing selector 902 outputs a signal of a predetermined period from a time point when light emission of the specific wavelength component (specifically, a wavelength component of laser beam) is detected (a period when the breakdown by laser is performed) as a signal 904, and outputs other signals to the signal splitter 708.

By analyzing with using this signal 904, it is possible to perform the analysis on the reaction at the time of laser ignition or the analysis by LIBS.

In FIG. 17, the processing selector 902 selects the output direction of the signal based on the signal from the spectrometer. However, the processing selector 902 may output, as the signal 904, a signal of a predetermined period from a time point when an external signal is received. For example, a trigger signal of laser radiation may be received. In an internal combustion engine of a spark ignition type or the reaction region where the reaction is initiated by discharge on a discharge electrode, when the optical element 104 is arranged towards a position where the discharge is performed and a measurement value of an electric current flowing to an ignition plug or the discharge electrode is given to the processing selector, it is possible to output a spectroscopic result of the light emission by the discharge as the signal 904. Thereby, the analysis on the light emission at the initial state of a flame kernel formation initiated by the discharge and the reaction analysis on the combustion reaction can be both performed. It is possible to perform both the analysis of SIBS forming the plasma by the discharge and the analysis of the reaction in the periphery thereof.

Figure 18:
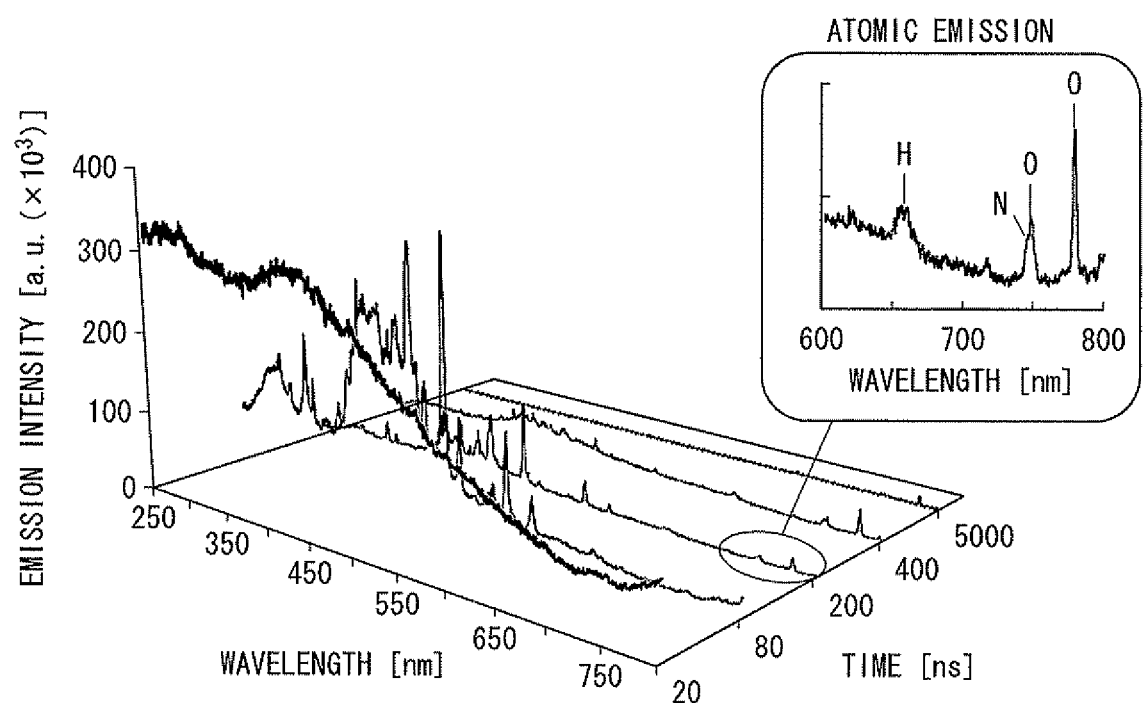
FIG. 18 A graph showing a spectral pattern generated in the case where LIBS (Laser Induced Breakdown Spectroscopy) is performed.

In the case where LIBS is performed, as shown in FIG. 18, braking radiation (radiation light generated due to rapid acceleration and deceleration of an electron) is generated at the initial stage thereof and a spectral pattern with high emission intensity is generated in accordance with shortening of the wavelength. When the relative intensity (supposing that the intensity on the side of short wavelength is the denominator) is calculated in such a case, it is thought that the relative intensity is decreased at the initial stage of LIBS, and then while moving to a spectral pattern of light due to breakdown of a component in the reaction region, the value is increased. Here, when the soot is generated after the breakdown and the ignition, the relative intensity becomes a further high value.

When the relative intensity is in a predetermined range or less, it is determined that the light emission is by the braking radiation, and the analysis of LIBS may be performed for the measurement result within the predetermined period after that.

In the case of the laser ignition, LIBS measurement is performed in a period from initial flame kernel formation after the braking radiation to the ignition, and after that, the processing such as the determination of the knocking and measurement of a flame zone may be executed.

It should be noted that in LIBS, a spectral pattern of light emission of an ion, a spectral pattern of light emission of an atom, and a spectral pattern of light emission of a molecule may be generated in this order over time after the generation of the braking radiation (particularly, in the case of LIBS for gas). In such a case, when an object to be analyzed is changed from the ion, the atom, the molecule and then the flame over time initiated by the braking radiation, it is possible to efficiently perform the analysis on the reaction region.

It should be noted that in the present modified example, LIBS or SIBS is performed in the combustion chamber as an example. However, LIBS and SIBS are not an analysis method limited to the analysis on the reaction region where the combustion is performed. For example, by inputting high energy to a surface of a solid or a liquid by the laser beam, the discharge or the like, it is possible to perform various analyses such as the componential analysis on the solid or the liquid and an analysis on a structure of a molecule or a crystal. By inputting further high energy to plasma with low energy density such as weakly-ionized plasma, it is possible to execute SIBS or LIBS targeting the plasma. Various known methods can be used for the processing of spectra in LIBS or SIBS. Processing functions thereof can be realized by a computer, data and a computer program. Therefore, it is possible to build a functional portion for performing the processing in the reaction analysis apparatus.

Modified Example 4

Relative Intensity

In the above embodiment, the intensity ratio between the first wavelength component and the second wavelength component is shown as the relative intensity as an example. However, the present invention is not limited to this. An angle between a straight line for connecting a position corresponding to the intensity value of the first wavelength component and a position corresponding to the intensity value of the second wavelength component and a wavelength axis (an inclination of an intensity change) on a spectral plane taking the wavelength and the intensity value as axes may be used instead of the relative intensity.

Modified Example 5

Control System

In the above embodiment, the measurement and the analysis on the reaction region are performed by the measurement system having the reaction analysis apparatus. However, an output from the measurement system with regard to the reaction region may be used as control of the reaction region.

For example, a control device having a conversion portion for converting the output by the measurement system into an input value corresponding to the output and serving as a controlled value mechanically by a function or by using a predetermined map, and further an adjustment portion for adjusting the reaction region so as to make a state corresponding to this input value may be used together with the measurement system. The input value may be a position, a path, an altitude, a posture, a direction, size, volume, an angle, a flow rate, density, linear speed, angular speed, acceleration, mechanical force, stress, fluid pressure, torque, amplitude, frequency, phase, a numerical quantity, a physicochemical variable quantity, a component, a mix ratio, humidity, a temperature, viscosity, an amount of light, color, electric charge, voltage, an electric current, magnetic flux density, a radiation dose or the like. For example, when the reaction region is of the internal combustion engine, the input value may be an inlet flow, inlet humidity, supply pressure of oxidant, a mix ratio of a component in the oxidant, amount of fuel supply, fuel supply speed, a fuel supply position, a fuel supply direction, fuel supply timing, a fuel grain diameter, a fuel penetration degree, a mixing degree, valve timing, relative time difference for opening and closing between valves, ignition timing, input energy for ignition, swirl strength, tumble strength, strength of disturbance of a working fluid in the vicinity of an ignition plug, the kind of a gauge to be operated, an quantity of the gauge to be operated, arrangement of the gauge to be operated, exhaust recirculation volume, a temperature of exhaust to be re-circulated, pressure of an exhaust pipe, afterburning, a qualitative component of the exhaust, a quantitative component of the exhaust, vibration of pressure wave or the like. The conversion from the output of the control system into the above input value and the adjustment of the state of the reaction region based on the input value can be realized by a control method generally performed for example with using an engine control unit (ECU), a carburetor or the like.

INDUSTRIAL APPLICABILITY

The present invention can be utilized for measurement and analysis of a reaction, error detection, reaction analysis and diagnosis and the like in general technologies of utilizing combustion, a plasma reaction or the like.

The invention claimed is:

1. A reaction analysis apparatus, comprising:
an optical element which receives light emitted by a reaction region and transmits the received light;
at least one spectrometer which receives the light transmitted by the optical element, converts the transmitted light into electric signals in accordance with intensities of various wavelength components and outputs the electric signals;
a computer which is programmed for:
obtaining an intensity value of a first wavelength component and an intensity value of a second wavelength component from the electric signals output by the spectrometer;
calculating relative intensity of the first wavelength component relative to the second wavelength component from the intensity value of the first wavelength component and the intensity value of the second wavelength component;
determining whether or not the calculated relative intensity is a value within a predetermined range;
selecting a wavelength range from a first wavelength range and a second wavelength range in accordance with the determination of whether or not the calculated relative intensity is within the predetermined range;
generating predetermined information on a characteristic of the reaction region based on a characteristic quantity of a peak within the wavelength range;
determining whether or not an unexpected combustion is generated based on timing appearance or on a temporal change of intensity of a peak at a fifth wavelength and at a sixth wavelength within the selected wavelength range and
generating information showing a result of the determination of whether or not an unexpected combustion is generated; and
an output device which notifies a user that a state of the reaction region is a predetermined state in response to a determination that the calculated relative intensity is within the predetermined range.

2. A reaction analysis apparatus, comprising:
an optical element which receives light emitted by a reaction region and transmits the received light;
at least one spectrometer which receives the light transmitted by the optical element, converts the transmitted light into electric signals in accordance with intensities of wavelength components and outputs the electric signals;
a computer which is programmed for:

obtaining an intensity value of a first wavelength component and an intensity value of a second wavelength component from the electric signals output by the spectrometer;

calculating relative intensity of the first wavelength component relative to the second wavelength component from the intensity value of the first wavelength component and the intensity value of the second wavelength component; and determining whether or not the calculated relative intensity is a value within a predetermined range;

selecting a wavelength range from a first wavelength range and a second wavelength range in accordance with the determination of whether or not the calculated relative intensity is within the predetermined range;

generating predetermined information on a characteristic of the reaction region based on a characteristic quantity of a peak within the selected wavelength range;

wherein the predetermined information includes information on pressure is generated and outputted based on width of peaks at two or more wavelengths within the selected wavelength range, and an output device which notifies a user that a state of the reaction region is a predetermined state in response to a determination that the calculated relative intensity is within the predetermined range.

3. A reaction analysis apparatus, comprising:

an optical element which is integrally formed so as to have a first surface and a second surface, and said first surface facing the reaction region, the first surface and the second surface having a first region and a second region respectively, wherein the first region of the first surface is a concave surface, wherein the first region of the second surface is a concave reflecting surface, wherein the second region of the first surface is a reflecting surface, and wherein the light incident from the reaction region is reflected on the first region of the second surface and the second region of the first surface so as to focus the light on an image point;

at least one spectrometer which receives the light transmitted by the optical element, converts the transmitted light into electric signals in accordance with intensities of wavelength components and outputs the electric signals;

a computer which is programmed for:

obtaining an intensity value of a first wavelength component and an intensity value of a second wavelength component from the electric signals output by the spectrometer;

calculating relative intensity of the first wavelength component relative to the second wavelength component from the intensity value of the first wavelength component and the intensity value of the second wavelength component;

determining whether or not the calculated relative intensity is a value within a predetermined range;

calculating a range of relative intensity and for distinguishing between and determining, as the state of the reaction region, thermal excitation emission, chemiluminescence and Bremsstrahlung in the reaction region, based on the calculated range of relative intensity; and an output device which notifies a user that a state of the reaction region is a predetermined state in response to a determination that the calculated relative intensity is within the predetermined range.

4. The reaction analysis apparatus according to claim 3, wherein:

the computer is further programmed for processing the electric signals from the spectrometer to analyze, in sequence, for an ion, an atom and a molecule in the reaction region when the computer determines that the state of the reaction region is Bremsstrahlung.

* * * * *